US009676825B2

(12) United States Patent
Dueñas Carrera et al.

(10) Patent No.: US 9,676,825 B2
(45) Date of Patent: Jun. 13, 2017

(54) CHIMERIC VACCINE ANTIGENS AGAINST HEPATITIS C VIRUS

(71) Applicant: Centro de Ingeniería Genética y Biotecnología, Havana (CU)

(72) Inventors: Santiago Dueñas Carrera, Havana (CU); Daylen Aguilar Noriega, Mayabeque (CU); Yalena Amador Cañizares, Havana (CU); Liz Alvarez-Lajonchere Ponce de León, Havana (CU); Gillian Martínez Donato, Havana (CU); Sonia Gonzalez Blanco, Havana (CU)

(73) Assignee: CENTRO DE INGENIERIA GENETICA Y BIOTECHNOLOGIA, La Habana (CU)

( * ) Notice: Subject to any disclaimer, the term of this patent is extended or adjusted under 35 U.S.C. 154(b) by 0 days.

(21) Appl. No.: 14/440,443

(22) PCT Filed: Oct. 28, 2013

(86) PCT No.: PCT/CU2013/000006
§ 371 (c)(1),
(2) Date: May 4, 2015

(87) PCT Pub. No.: WO2014/067498
PCT Pub. Date: May 8, 2014

(65) Prior Publication Data
US 2015/0307558 A1 Oct. 29, 2015

(30) Foreign Application Priority Data

Nov. 5, 2012 (CU) .................................. 2012-0153

(51) Int. Cl.
| | |
|---|---|
| *A61K 39/12* | (2006.01) |
| *C12N 7/00* | (2006.01) |
| *C07K 14/005* | (2006.01) |
| *A61K 39/29* | (2006.01) |
| *C07K 7/08* | (2006.01) |
| *A61K 39/00* | (2006.01) |

(52) U.S. Cl.
CPC ............ *C07K 14/005* (2013.01); *A61K 39/12* (2013.01); *A61K 39/29* (2013.01); *C07K 7/08* (2013.01); *C12N 7/00* (2013.01); *A61K 39/00* (2013.01); *A61K 2039/53* (2013.01); *A61K 2039/55505* (2013.01); *C12N 2770/24234* (2013.01); *C12N 2770/24271* (2013.01)

(58) Field of Classification Search
CPC .......... C12N 2770/24222; C12N 2770/24211; C12N 2770/24262; C07K 16/109; C12Q 1/707; C12Q 1/34; C12Q 2600/158; G01N 33/5767; G01N 2333/186; A61K 39/12; A61K 39/29; A61K 2039/525
See application file for complete search history.

(56) References Cited

U.S. PATENT DOCUMENTS

2011/0256098 A1   10/2011   Apelian et al.

FOREIGN PATENT DOCUMENTS

| EP | 1785143 A2 | 5/2007 |
| WO | WO0137869 A1 | 5/2001 |
| WO | WO2007081868 A2 | 7/2007 |
| WO | WO2009056535 A2 | 5/2009 |

OTHER PUBLICATIONS

Alvarez-Lajonchere et al., "Complete Definition of Immunological Correlates of Protection and Clearance of Hepatitis C Virus Infection: A Relevant Pending Task for Vaccine Development," International Reviews of Immunology, vol. 31, pp. 223-242, 2012.
Alvarez-Lajonchere et al., "Advances in DNA immunization against hepatitis C virus infection," Human Vaccines vol. 5:8, pp. 1-4, Aug. 2009.
Amoroso et al., "Correlation between virus genotype and chronicity rate in acute hepatitis C," Journal of Hepatology vol. 28, pp. 939-944, 1998.
Alvarez-Lajonchere et al., "Generation and characterization of recombinant vaccinia viruses expressing a hepatitis C virus Core protein, genotype 1 b, individually or as a polyprotein," Biotechnologia Aplicada, vol. 24, pp. 246-253, 2007.
Lorenzo et al., "Expression and immunological evaluation of the *Escherichia coli*-derived hepatitis C virus envelope E1 protein," Biotechnol. Appl. Biochem., vol. 32, pp. 137-143, 2000.
Alvarez-Lajonchere et al., "Immunization with a recombinant fowlpox virus expressing a hepatitis C virus core-E1 polyprotein variant, protects mice and African green monkeys (Chlorocebus aethiops sabaeus) against challenge with a surrogate vaccinia virus," Biotechnol. Appl. Biochem. vol. 51, pp. 97-105, 2008.
Barnes et al., "Novel Adenovirus-Based Vaccines Induce Broad and Sustained T Cell Responses to HCV in Man," Science Translation Medicine, vol. 4, 115ral, 2012.
Bartenschlager et al., "Replication of hepatitis C virus," Journal of General Virology vol. 81, pp. 1631-1648, 2000.
Dueñas-Carrera et al., "Variable Level Expression of Hepatitis C Virus Core Protein in a Prokaryotic system. Analysis of the Humoral Response against it in Rabbits," Biotecnologia Aplicada, vol. 16, pp. 226-231, 1999.
Bruña-Romero et al., "Induction of Cytotoxic T-Cell Response Against Hepatitis C Virus Structural Antigens Using a Defective Recombinant Adenovirus," Hepatology, vol. 25. No. 2, 1997.

(Continued)

*Primary Examiner* — Bao Li
(74) *Attorney, Agent, or Firm* — Hoffmann & Baron, LLP

(57) ABSTRACT

The invention relates to chimeric vaccine antigens against hepatitis C virus (HCV) comprising selected regions of different antigens of said virus, which are placed in a pre-determined order inside the polypeptide. In addition, said chimeric antigens can include artificially formed specific epitopes for auxiliary T helper lymphocytes. The chimeric antigens and the resulting vaccine compositions are suitable for use in medicine and the pharmaceutical industry, as well as being suitable for prophylactic and/or therapeutic use against HCV. The vaccine compositions of the invention generate a powerful, broad-spectrum immune response against different antigens of the virus, with a minimum number of components.

16 Claims, 10 Drawing Sheets

(56) References Cited

OTHER PUBLICATIONS

Castellanos et al., "Immunization with a DNA vaccine candidate in chronic hepatitis C patients is safe, well tolerated and does not impair immune response induction after anti-hepatitis B vaccination," The Journal of Gene Medicine, vol. 12, pp. 107-116, 2010.
Choo et al., "Vaccination of chimpanzees against infection by the hepatitis C virus," Proc. Natl. Acad. Sci. USA, vol. 91, pp. 1294-1298, Feb. 1994.
Simmonds et al., "Genetic diversity and evolution of hepatitis C virus—15 years on," Journal of General Virology, vol. 85, pp. 3173-3188, 2004.
Fournillier et al., "An accelerated vaccine schedule with a polyantigenic hepatitis C virus MVA-based candidate vaccine induces potent, long lasting and in vivo cross-reactive T cell responses," Vaccine, vol. 25, pp. 7339-7353, 2007.
González-Horta et al., "Analysis of hepatitis C virus core encoding sequences in chronically infected patients reveals mutability, predominance, genetic history and potential impact on therapy of Cuban genotype 1b isolates," European Review for Medical and Pharmacological Sciences, vol. 15, pp. 1320-1327, 2011.
Grakoui et al., "HCV Persistence and Immune Evasion in the Absence of Memory T Cell Help," Science Magazine, vol. 302, pp. 659-662, 2003.
Ghany et al., "Diagnosis, Management, and Treatment of Hepatitis C: An Update," AASLD Practice Guidelines, Hepatology, vol. 49, No. 4, pp. 1335-1374, 2009.
Hiranuma et al., "Helper T cell determinant peptide contributes to induction of cellular immune responses by peptide vaccines against hepatitis C virus," Journal of General Virology, vol. 80, pp. 187-193, 1999.
Hoofnagle, J., "Course and Outcome of Hepatitis C," Hepatology, vol. 36, No. 5, Suppl. 1, pp. 521-529, 2002.
Yero et al., "Bicistronic expression plasmid for the rapid production of recombinant fused proteins in *Escherichia coli*," Biotechnol. Appl. Biochem. vol. 44, 2006.
Yutani et al., "Phase I clinical study of a peptide vaccination for hepatitis C virus-infected patients with different human leukocyte antigen-class I-A alleles," Cancer Science, vol. 100, No. 10, pp. 1935-1942, Oct. 2009.
Klade et al., "Therapeutic Vaccination of Chronic Hepatitis C Nonresponder Patients With the Peptide Vaccine IC41," Gastroenterology, vol. 134, No. 5, pp. 1385-1395, 2008.
Large et al., "Suppression of Host Immune Response by the Core Protein of Hepatitis C Virus: Possible Implications for Hepatitis C Virus Persistence," The Journal of Immunology, vol. 162, pp. 931-938, 1999.
Makimura et al., "Induction of antibodies against structural proteins of hepatitis C virus in mice using recombinant adenovirus," Vaccine, vol. 14 No. 1, pp. 26-34, 1996.
Martínez-Donato et al., "Multimeric HCV E2 Protein Obtained From Pichia pastoris Cells Induces a Strong Immune Response in Mice," Molecular Biotechnology, vol. 35, 2007.
Nevens et al., "A Pilot Study of Therapeutic Vaccination With Envelope Protein E1 in 35 Patients With Chronic Hepatitis C," Hepatology, vol. 38, pp. 1289-1296, 2003.
Oseroff, et al., "Pools of lipidated HTL-CTL constructs prime for multiple HBV and HCV 1CTL epitope responses," Vaccine, vol. 16. No. 8, pp. 823-833, 1998.
Palenzuela, et al., "A new NS3 recombinant protein shows improved antigenic properties for HCV diagnosis," Biotecnologia Aplicada, vol. 23, pp. 94-98, 2006.
Dueñas-Carrera et al., "Immunization with a DNA vaccine encoding the hepatitis-Cvirus structural antigens elicits a specific immune response against the capsid and envelope proteins in rabbits and Macaca irus (crab-eating macaque monkeys)," Biotechnol. Appl. Biochem., vol. 39, pp. 249-255, 2004.
Rosa, et al., "A quantitative test to estimate neutralizing antibodies to the hepatitis C virus: Cytofluorimetric assessment of envelope glycoprotein 2 binding to target cells," Proc. Natl. Acad. Sci. USA, vol. 93, pp. 1759-1763, 1996.
Shirai et al., "An Epitope in Hepatitis C Virus Core Region Recognized by Cytotoxic T Cells in Mice and Humans," Journal of Virology, vol. 68, No. 5, pp. 3334-3342, 1994.
Simmonds, P., "Viral heterogeneity of the hepatitis C virus," Journal of Hepatology, vol. 31, pp. 54-60, 1999.
Cesar Alvarez-Obregón et al., "A truncated HCV core protein elicits a potent immune response with a strong participation of cellular immunity components in mice," Vaccine, vol. 19, pp. 3940-3946, 2001.
Williams, R., "Global Challenges in Liver Disease," Hepatology, vol. 44, No. 3, pp. 521-526, 2006.
Arashkia et al., "Construction of HCV-polytope vaccine candidates harbouring immune-enhancer sequences and primary evaluation of their immunogenicity in BALB/c mice," Virus Genes, vol. 40, pp. 44-52, 2010.
Shirai et al, "Use of Intrinsic and Extrinsic Helper Epitopes for In Vivo Induction of AntiHepatitis C Virus Cytotoxic T Lymphocytes (CTL) with CTL Epitope Peptide Vaccines," The Journal of Infectious Diseases, vol. 173, pp. 24-31, 1996.
Sällberg et al., "DNA vaccine therapy for chronic hepatitis C virus (HCV) infection: immune control of a moving target," Expert Opin. Biol. Ther. vol. 9(7), pp. 805-815, 2009.
Lechmann, et al., "Vaccine Development for Hepatitis C," Seminars in Liver Disease, vol. 20, No. 2, pp. 211-226, 2000.
Maertens, et al., "Improvement of chronic active hepatitis C in chronically infected chimpanzees after therapeutic vaccination with the HCV E1 protein," Acta Gastro-Enterologica Belgica, vol. 63, Apr.-Jun. 2000.

A

Coq1
276 aa

B

Eq1
276 aa

C

E1q1
276 aa

D

NSEq2
333 aa

E

EqNSb
341 aa

F

EqNS3
454 aa

G

EqP1
292 aa

H

Eq1b
276 aa

CHIMERIC VACCINE ANTIGENS AGAINST HEPATITIS C VIRUS

This application is the U.S. National Phase of, and Applicant claims priority from, International Patent Application Number PCT/CU2013/000006 filed Oct. 28, 2013, which claims priority from CU 2012-0153 filed Nov. 5, 2012, each of which is incorporated herein by reference.

TECHNICAL FIELD

The current invention is related to the medical field and the pharmaceutical industry, particularly, to the development of chimeric antigens against hepatitis C virus (HCV) and vaccine compositions that comprise them. In this invention, a minimal number of components are used because the precise selection of specific regions of HCV antigens and the inclusion of artificial epitopes, specific to CD4+ T lymphocytes, enables chimeric antigens to induce a potent and broad immune response against HCV.

BACKGROUND OF THE INVENTION

HCV infects around 3% of worldwide population (Williams R. Hepatology 2006; 44: 521-526). Most of the infected individuals evolve to chronicity (Amoroso P, y cols., J Hepatol 1998; 28: 939-944). Hepatitis C infection is one of the principal causes of chronic hepatic damage, cirrhosis, liver failure and liver cancer (Hoofnagle J H. Hepatology 2002; 36 (5 Suppl 1): S21-S29). Currently, HCV infection is the principal cause of liver transplantation in first world countries. Additionally, HCV infection has been related with extra-hepatic manifestations as type II cryoglobulinemia, membranoproliferative glomerulonephritis, porphyria cutanea tarda, among others. At present, a preventive vaccine against this virus is not available and the conventional antiviral treatments in use, based on the combination of pegylated interferon (IFN)+ribavirin, are effective in less than 50% of cases. Furthermore, the aforementioned treatments cause multiples adverse events (Ghany M G y cols., Hepatology. 2009; 49 (4):1335-74).

HCV belongs to the *Hepacivirus* genus of the Flaviviridae family. It is an enveloped virus, which viral particles are around 50 and 70 nm in diameter and are associated to very low density lipoproteins (VLDL) (Popescu C I y Dubuisson J. Biol Cell. 2009; 102 (1):63-74). The viral genome is a positive stranded ribonucleic acid (RNA) of approximately 9.6 kb. The genome encodes for a viral polyprotein that is processed co- and post-translationally in at least 10 viral proteins: Core, E1, E2, p7 (structural proteins) and nonstructural proteins: NS2, NS3, NS4A, NS4B, NS5A, NS5B (Bartenschlager R y Lohmann V. 2000. J Gen Virol. 81: 1631-48).

There are several important obstacles to the development of an effective vaccine against HCV. This pathogen is an RNA virus that can rapidly mutate adapting to the host environment. This contributes to the high diversity of the multiple viral isolates identified worldwide. Six major HCV genotypes have been identified, which can differ up to 30% in nucleotide sequence (Simmonds P. J Hepatol. 1999; 31 Suppl 1:54-60). The greatest heterogeneity is observed in the hypervariable region of HCV E2 protein, where an epitope potentially targeted by neutralizing antibodies is found. In fact, HCV circulates in the body as a heterogeneous population of viral molecules, this phenomenon is known as quasiespecies (Simmonds P. J Gen Virol. 2004; 85 (Pt 11):3173-88). It has been demonstrated that mutations constitute a way of viral escape to specific humoral and cellular immune response developed by the host.

It should be stressed that HCV causes persistent infection in immunocompetent individuals, despite the occurrence of an active immune response (Lechmann et al., Semin Liver Dis 2000, 20, 211-226). Currently, several viral effects that contribute to the persistence of the infection, by encouraging irrelevant immune responses and preventing an effective immune response, have been elucidated. These effects are detected over both innate and acquired immunity (Grakoui A y cols. Science 2003, 302 (5645): 659-62). There are evidences supporting that an ineffective immune response against HCV, not only fails to eliminate this pathogen, but it also contributes to liver damage.

So far, the immunological parameters that correlate with protection and clarification against HCV have not been completely defined. However, the induction of potent and sustained cellular immune response against different HCV antigens is considered particularly relevant (Lechmann et al., Semin Liver Dis 2000, 20, 211-226). In HCV chronically infected patients the impairment of the specific T lymphocyte response is particularly significant. Several mechanisms seem to contribute to this effect; one of them is the action of regulatory T cells.

Almost all immunization strategies have been attempted to develop a vaccine against HCV. Some of those strategies include: recombinant proteins, synthetic peptides, virus like particles, naked deoxyribonucleic acid (DNA) and recombinant viruses. All viral antigens have been evaluated as targets in vaccine candidates against HCV. Most of the vaccine candidates are at the stage of immunogenicity studies in animal models. Nevertheless, at present some candidates have reached clinical evaluation, they have demonstrated to be safe and immunogenic, but a clear clinical impact has not been demonstrated yet (Alvarez-Lajonchere L, Dueñas-Carrera S. Int Rev Immunol. 2012; 31(3):223-42).

The development of a subunit protein vaccine candidate was one of the first strategies evaluated to obtain an HCV vaccine. Some of those candidates based on structural antigens have achieved limited protection against viral challenges in animal models. Such is the case of chimpanzees immunized with an E1 and E2 oligomer. Seven chimpanzees were immunized, five of them became protected and two became infected, but then cleared the virus without reaching chronicity (Choo y cols., Proc Natl Acad Sci USA 1994, 91, 1294-1298). This protection correlated with the presence of antibodies able to inhibit the interaction between E2 protein and human cells (Rosa y cols., Proc Natl Acad Sci USA 1996, 93, 1759-1763).

A recombinant E1 protein, from a 1 b genotype isolate, was purified as homodimers (Maertens y cols., Acta Gastroenterol Belg 2000, 63, 203). Two chimpanzees chronically infected with HCV received 9 doses of 50 μg of this recombinant E1 protein. Vaccination improved liver histology, cleared viral antigens from the liver and reduced alanine aminotransferase levels. However, serum RNA levels did not change during treatment and hepatic inflammation and viral antigens reappeared after treatment conclusion. An association between high anti-E1 antibodies levels and liver damage reduction was observed (Maertens et al., Acta Gastroenterol Belg 2000, 63, 203). An E1 protein variant formulated in alum was evaluated in humans. This candidate was safe and immunogenic, inducing specific antibodies and linfoproliferative responses (Nevens F, y col., Hepatology. 2003; 38 (5):1289-96). However, the administration of this candidate did not affect the clinical course of HCV infection, as patients did not clear the virus, and no liver histological improvement was observed. The protein subunits approach, as a disadvantage, has not induced a strong cellular immune response in some cases. This approach may have another drawback: the insertion of regions involved in the different mechanisms of HCV-specific immune response impairment induced by the pathogen at different levels (Grakoui A y cols., Science 2003, 302 (5645): 659-62).

Two vaccine candidates based on mixtures of synthetic peptides, including T lymphocytes epitopes, have also reached clinical trials (Yutani y cols., Cancer Sci 2009.100 (10): 1935-42, Klade y cols., Gastroenterology 2008.134(5): 1385-95). Both candidates induced specific immune responses and had low reactogenicity in HCV chronically infected patients during Phase I and II clinical trials conducted so far (Alvarez-Lajonchere L, Dueñas-Carrera S. Int Rev Immunol. 2012; 31 (3):223-42). Nevertheless, these vaccine candidates have not shown significant effect on viral load or have had a transient effect. Taking into account that these candidates have not induced any improvement over liver histology, their clinical impact is still to be demonstrated. Different epitopes for CD4+ and CD8+ T cells that might be important for viral clearance have been identified throughout HCV polyprotein. These findings support the synthetic peptides based vaccine strategy. Different peptides including Core, NS4 and NS5 epitopes, alone or with lipids moieties, have induced strong T cytotoxic responses in mice (Shirai et al., J Infect Dis 1996, 173, 24-31; Hiranuma et al., J Gen Virol 1999, 80, 187-193; Oseroff et al., Vaccine 1998, 16, 823-833). The principal disadvantage of this approach is that those peptides without T helper function may be poor immunogens. In addition, the efficacy of a vaccine depends frequently on the induction of a multivalent and broad spectrum immune response against several antigens. As the number of peptides included in a vaccine increases, the formulation complexity rises from all viewpoints. These limitations are weaknesses of this approach.

On the other hand, different recombinant viral vectors have been evaluated as vaccine candidates for HCV. Defective recombinant adenoviruses are attractive candidates, due to their liver tropism, their capacity to induce humoral and cellular immune responses and the possibility to be administered by oral and parenteral routes. Recombinant adenoviruses expressing HCV structural proteins induce antibodies responses against each of these proteins (Makimura et al., Vaccine 1996, 14, 28-36). Besides, after mice immunization with Core and E1 recombinant adenovirus, a specific T cytotoxic immune response is detected against these antigens (Bruna-Romero et al., Hepatology 1997, 25, 470-477). Although these are encouraging results; some problems related to the use of recombinant adenoviruses in gene therapy have raised doubts about their safety in humans. At present, a vaccine candidate based on HCV recombinant adenovirus is being evaluated in clinical trials with good results on immunogenicity, but without evidence of clinical impact (Barnes y cols., Sci Transl Med. 2012; 4(115): 115). The use of others recombinant viral vectors, such as vaccinia, fowlpox and canarypox containing different HCV genes have induced strong T cytotoxic and helper responses in mice (Shirai et al., J Virol 1994, 68, 3334-3342; Large et al., J Immunol 1999, 162, 931-938). Particularly, a modified vaccinia virus Ankara, recombinant for HCV nonstructural antigens NS3-NS5, has been evaluated in clinical trials in humans (Fournillier y cols., Vaccine. 2007; 25 (42):7339-53). This candidate was immunogenic and well tolerated in a phase I clinical trial in HCV chronically infected patients. Similar to the peptide approach, the effect over de viral load was transient and observed only in a fraction of the vaccinees; therefore, the clinical impact is still to be demonstrated. In general, the vaccine candidates based on recombinant viruses are hampered by safety and regulatory issues related with their application. DNA immunization has been extensively studied as a strategy for HCV vaccine development. Studies in animal models have showed the capacity of these candidates to induce cellular and humoral immune responses against almost all HCV antigens (Alvarez-Lajonchere L, Dueñas-Carrera S, Hum Vaccin. 2009; 5 (8):568-71). Two vaccine candidates that include DNA immunization plasmids containing sequences encoding HCV antigens are in clinical trials in humans (Alvarez-Lajonchere L, Dueñas-Carrera S, Int Rev Immunol. 2012; 31 (3):223-42). In one case, it is a DNA vaccine expressing NS3 to NS5 proteins, administered by electroporation (Sällberg M, y cols., Expert Opin Biol Ther. 2009; 9 (7):805-15). In the other case, it is a vaccine composition based on the mixture of a recombinant core protein and a DNA plasmid that expresses HCV structural antigens (Castellanos M, y cols., J Gene Med. 2010; 12 (1):107-16). Both candidates have demonstrated to be safe, well tolerated and have induced specific immune responses in immunized subjects (Alvarez-Lajonchere L, Dueñas-Carrera S, Int Rev Immunol. 2012; 31 (3):223-42). In neither of these two cases, the effect over HCV infection course or a sustained histological improvement, have been demonstrated. DNA vaccines, despite their potential advantages related to their simplicity and stability, face important regulatory challenges. Their principal limitation seems to be related to their insufficient immunogenicity in humans, phenomenon not completely understood so far, and that differs considerably with the results obtained in animal models.

According to the aforementioned elements, the development of a prophylactic or therapeutic vaccine against HCV is an unsolved problem. The present invention is directed precisely towards this goal.

DESCRIPTION OF THE INVENTION

The present invention solves the aforementioned problem providing a chimeric vaccine antigen against hepatitis C virus (HCV) which comprises: a) a first segment corresponding to E2 region (amino acids 408-540) of HCV polyprotein, b) a second segment corresponding to E1 region (amino acids 190-222) of HCV polyprotein, and c) a third segment corresponding to Core region (amino acids 1-50) of HCV polyprotein, in that order.

The novelty of the invention lies on the specific selection of epitopes and the order in which they are placed on the generated protein variants. This vaccine antigen's design makes possible to reduce the number of components needed to broaden and potentiate the immune response spectrum against different HCV antigens. The present invention describes, for the first time, a fusion protein comprising in a single chimeric antigen HCV polyprotein regions corresponding to E2 (amino acids 408-540), E1 (amino acids 190-222) and Core (amino acids 1-50) particularly in that order. The resulting immune response is relevant and it is directed, therefore, against a wide spectrum of viral antigens.

The selection of specific regions of HCV avoids the use of those regions from viral proteins that may exert immune suppressive effects. Likewise it avoids the use of other regions that may be immune dominant over those selected in the present invention and which, if included in the designed antigen, would limit the induction of specific immune response against the regions selected in the present invention. On the other hand, the invention includes the order in which the selected regions are placed in the artificial protein antigen, given the fact that this element significantly influences the induction of the immune response against HCV, due to differences in epitope exposition and processing/presentation to the immune system. In fact, in the chimeric antigens of the present invention the regions from core, E1 and E2 proteins are placed in inverse order respecting that of the native viral polyprotein.

In a realization of the invention, the sequence of the chimeric vaccine antigen is selected among the group composed of SEQ ID No. 10 (Eq1antigen) and SEQ ID No. 16 (Eq1b antigen).

The chimeric antigens of the invention may additionally include in their sequence at least one T helper lymphocyte-specific epitope. In a materialization of the invention, the T helper lymphocyte-specific epitope included in the chimeric antigens is one epitope from HCV nonstructural proteins. In a particular realization, the nonstructural protein is NS3. More particularly, the invention provides a chimeric vaccine antigen characterized by the amino acid sequence identified as SEQ ID No. 14 (EqNS3 antigen).

In other aspect of the invention, the T helper lymphocyte-specific epitope included in the chimeric antigens is a CD4+ T lymphocyte artificial epitope. In the context of the invention, the term artificial epitope defines an epitope which amino acid sequence does not exist in a natural form; instead it is designed by bioinformatics. The selection and inclusion of the artificial epitopes, which are recognized by T helper lymphocytes, contributes to the induction of a specific immune response against the HCV epitopes included in the chimeric antigenic variants. For the first time, this invention describes as artificial epitopes for T helper lymphocytes epitopes P1M (SEQ ID No. 17) and P2B (SEQ ID No. 18). These epitopes were designed to contain an HLA-DR13 and HLA-DR11 binding motive. Therefore, the invention provides a T helper lymphocyte specific epitope which amino acid sequence corresponds to that identified as SEQ ID No. 17 or SEQ ID No. 18.

In a materialization of the invention the chimeric antigens contain an amino acid sequence which is selected from the group composed of SEQ ID No. 12 (NSEq2 antigen), SEQ ID No. 13 (EqNSb antigen) and SEQ ID No. 15 (EqP1 antigen), and they contain at least one of these T helper lymphocyte specific epitopes.

The following chimeric antigens have the characteristics summarized below: The chimeric antigen Eq1 (SEQ ID No. 10) comprises the regions E2 (amino acids 408-540), E1 (amino acids 190-222) and Core (amino acids 1-50) of the HCV polyprotein in that particular order. The chimeric antigen NSEq2 (SEQ ID No. 12) includes epitopes P2B and P1M, in that order, inserted on Eq1, between E1 (amino acids 190-222) and Core (amino acids 1-50) regions. The chimeric antigen EqNSb (SEQ ID No. 13) includes P2B epitope inserted on Eq1 between E1 (amino acids 190-222) and Core (amino acids 1-50) regions. The chimeric antigen EqNS3 (SEQ ID No. 14) includes amino acid regions 1242-1415 of the HCV polyprotein inserted on Eq1, between E1 (amino acids 190-222) and Core (amino acids 1-50) regions. The chimeric antigen EqP1 (SEQ ID No. 15) includes P1M epitope, inserted in Eq1, between E1 (amino acids 190-222) and Core (amino acids 1-50) regions. The chimeric antigen Eq1b (SEQ ID No. 16) comprises E2 (amino acids 408-540), E1 (amino acids 190-222) and Core (amino acids 1-50) regions of HCV polyprotein, in that particular order, but in that case the amino acids sequence corresponds to HCV genotype 1a H77 variant (NCBI Reference Sequence: NC_004102.1).

In a materialization of the invention, the chimeric antigens were obtained by recombinant DNA technology, from bacteria transformed with the plasmids described in Example 1. Nevertheless, experts in this technique know that such antigens may be obtained from other hosts and may be purified by widely known procedures, to be used for immunization.

In another aspect, the invention provides a vaccine composition comprising a chimeric vaccine antigen against HCV which is composed of a) a first segment consisting of E2 region (amino acids 408-540) of HCV polyprotein, b) a second segment consisting of E1 region (amino acids 190-222) of HCV polyprotein and c) a third segment consisting of Core region (amino acids 1-50) of HCV polyprotein, in that order; and pharmaceutically acceptable excipients and/or adjuvants.

In a materialization of the invention, the vaccine composition comprises the antigens identified as SEQ ID No. 10 (Eq1 antigen), SEQ ID No. 16 (Eq1b antigen), SEQ ID No. 14 (EqNS3 antigen), SEQ ID No. 12 (NSEq2 antigen), SEQ ID No. 13 (EqNSb antigen) or SEQ ID No. 15 (EqP1 antigen).

For the purposes of the invention, a wide range of pharmaceutically acceptable adjuvants, which are commercially available or those on development stages, may be used to potentiate the immune response against the chimeric antigens contained in the vaccine compositions object of the invention.

The vaccine compositions of the invention may as well comprise a recombinant protein variant of HCV structural or NS3 antigens. Additionally, the vaccine compositions of the invention may comprise a plasmid for DNA immunization, which expresses HCV structural antigens. In another realization of the invention, the chimeric antigens may be formulated with a plasmid for DNA immunization, which expresses HCV structural antigens and a HCV recombinant capsid protein, simultaneously.

In another aspect, the invention includes that the vaccine composition which comprises a vaccine chimeric antigen against HCV including: a) a first segment consisting of E2 region (amino acids 408-540) of HCV polyprotein, b) a second segment consisting of E1 region (amino acids 190-222) of HCV polyprotein and c) a third segment consisting of Core region (amino acids 1-50) of HCV polyprotein, in that order, may be administered on prime/boost schedules, along with preparations based on plasmids for DNA immunization, recombinant variants of HCV structural proteins or a mixture of both.

The vaccine compositions which are objects of the present invention have the advantage of inducing both humoral and cellular immune responses against several HCV antigens, therefore they are active against a wide spectrum of viral isolates and are capable of inducing protection in a surrogate viral challenge model.

In the invention, the vaccine compositions may be administered by the intramuscular, intradermal, intraperitoneal, subcutaneous, intramucosal, intravenous or sublingual routes, or any other route known by experts in the field. On the other hand, the administration may be by means of syringes, spray or any other administration devises.

It is also the object of the invention the use of the chimeric vaccine antigens composed of a first segment consisting of E2 region (amino acids 408-540) of HCV polyprotein, a second segment consisting of E1 region (amino acids 190-

222) of HCV polyprotein and a third segment consisting of Core region (amino acids 1-50) of HCV polyprotein, in that order, for the fabrication of a vaccine to induce of an immune response against HCV. In a materialization of the invention, the aforementioned vaccine is capable of inducing protection in vivo in a surrogate viral challenge model. On the other hand, the vaccines of the invention are capable of inducing responses in healthy individuals or in HCV infected patients. Therefore, it is also an aspect of the invention to provide a method for the induction of immune response against HCV. This method is characterized by the administration of the chimeric antigen composed of a first segment consisting of E2 region (amino acids 408-540) of HCV polyprotein, a second segment consisting of E1 region (amino acids 190-222) of HCV polyprotein and a third segment consisting of Core region (amino acids 1-50) of HCV polyprotein, in that order, or a vaccine composition which contains the aforementioned antigen, to a healthy or HCV infected individual.

The invention also includes that in the aforementioned method, the chimeric vaccine antigen, or the vaccine composition that contains it, is administered on prime/boost schedules with preparations based on plasmids for DNA immunization, recombinant variants of HCV structural antigens or a mixture of both.

For the treatment of HCV infected patients, the antigens of the invention or the vaccine compositions that contain them may be administered simultaneously with the medicaments included on the standard of care for this type of patients.

DETAILED EXPOSITION OF THE EXPERIMENTAL MODES/EXAMPLES OF PERFORMANCE

Example 1. Generation of Different Chimeric Antigens Including HCV Epitopes

Figure 1:
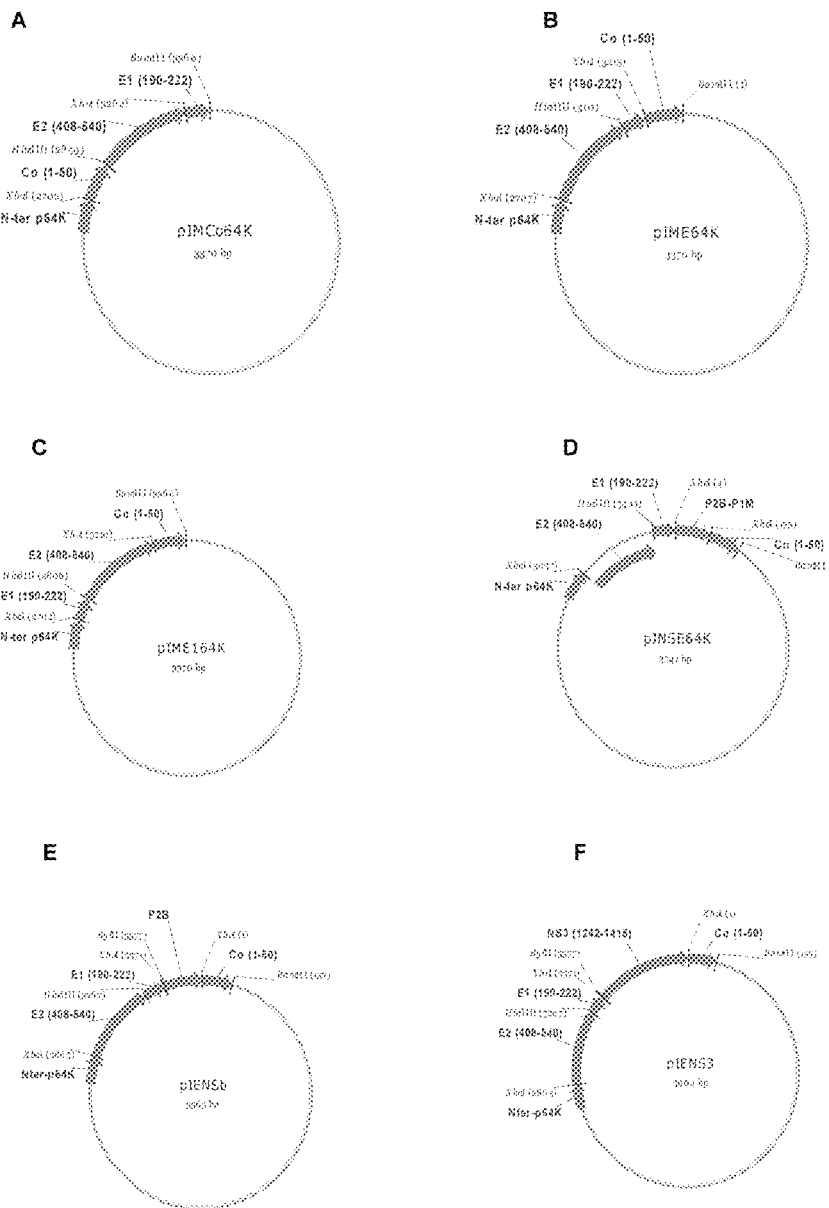
FIG. 1. Maps of the plasmids that contain the sequences encoding the different chimeric antigens. A: pIMCo64K, plasmid for the expression of Coq1 antigen. B: pIME64K, plasmid for the expression of Eq1 antigen. C: pIME164K, plasmid for the expression of E1q1 antigen. D: pINSE64K, plasmid for the expression of NSEq2 antigen. E: pIENSb, plasmid for the expression of EqNSb antigen. F: pIENS3, plasmid for the expression of EqNS3 antigen. G: pIMP1E64K, plasmid for the expression of EqP1 antigen. H: pIME64Kb, plasmid for the expression of Eq1b antigen.
Figure 1:
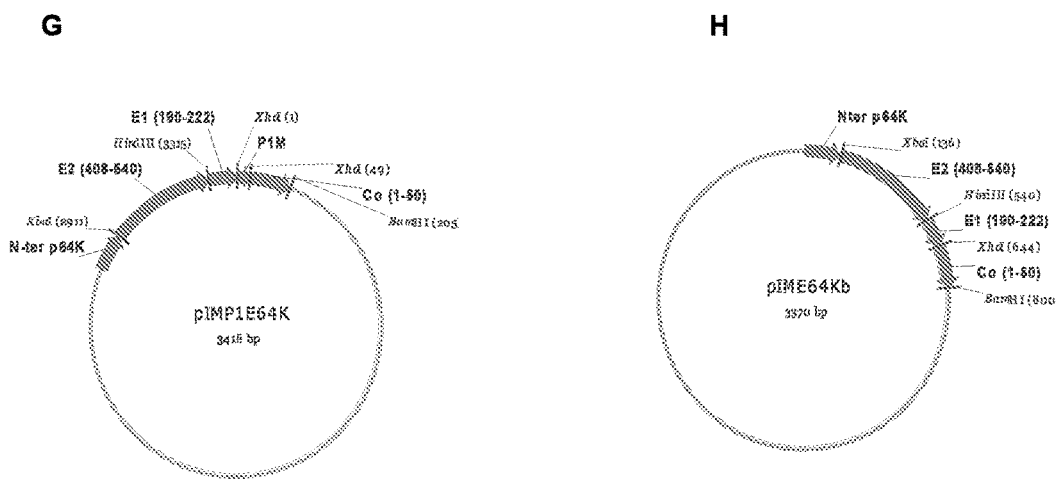

As shown in FIG. 1, plasmids pIMCo64K (SEQ ID No. 1), pIME64K (SEQ ID No. 2), pIME164K (SEQ ID No. 3), pINSE64K (SEQ ID No. 4), pIENSb (SEQ ID No. 5), pIENS3 (SEQ ID No. 6), pIMP1E64K (SEQ ID No. 7), pIME64Kb (SEQ ID No. 8) were obtained. These plasmids allow the expression in *Escherichia coli* of the chimeric antigens Coq1 (SEQ ID No. 9), Eq1 (SEQ ID No. 10), E1q1 (SEQ ID No. 11), NSEq2 (SEQ ID No. 12), EqNSb (SEQ ID No. 13), EqNS3 (SEQ ID No. 14), EqP1 (SEQ ID No. 15) and Eq1b (SEQ ID No. 16), respectively, represented in FIG. 2. In all cases, with the exception of the antigen Eq1b (which sequence comes from the HCV strain H77, genotype 1a), the amino acids sequence comes from a HCV genotype 1b isolate (González-Horta E E, Eur Rev Med Pharmacol Sci. 2011; 15 (11): 1320-7).

Figure 2:
FIG. 2. Schematic representation of the different chimeric antigens. A: Coq1 antigen, comprises Core (amino acids 1-50), E1 (amino acids 190-222) and E2 (amino acids 408-540) regions of HCV polyprotein. B: Eq1 antigen, comprises E2 (amino acids 408-540), E1 (amino acids 190-222) and Core (amino acids 1-50) of HCV polyprotein. C: E1q1 antigen, comprises E1 (amino acids 190-222), E2 (amino acids 408-540), and Core (amino acids 1-50) of HCV poliprotein. D: NSEq2 antigen, includes P2B and P1M epitopes, inserted on Eq1 between E1 (amino acids 190-222) and Core (amino acids 1-50) regions. E: EqNSb antigen, includes P2B epitope inserted on Eq1, between E1 (amino acids 190-222) and Core (amino acids 1-50) regions. F: EqNS3 antigen, includes amino acids region 1242-1415 of HCV polyprotein, inserted between E1 (amino acids 190-222) and Core (amino acids 1-50) regions on Eq1. G: EqP1 antigen, includes P1M epitope inserted on Eq1, between E1 (amino acids 190-222) and Core (amino acids 1-50) regions. H: Eq1b antigen, comprises E2 (amino acids 408-540), E1 (amino acids 190-222) and Core (amino acids 1-50) regions of genotype 1a H77 variant of HCV polyprotein.
Figure 2:
Figure 2:
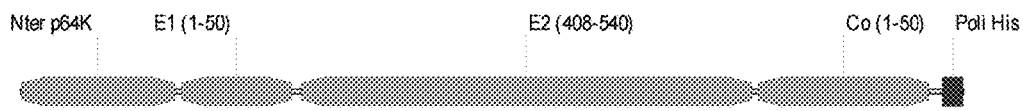
Figure 2:
Figure 2:
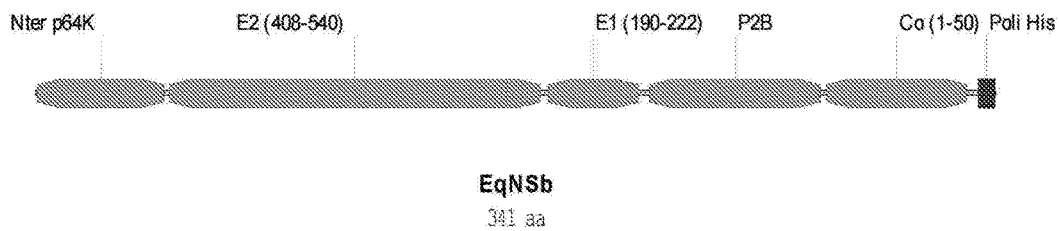
Figure 2:
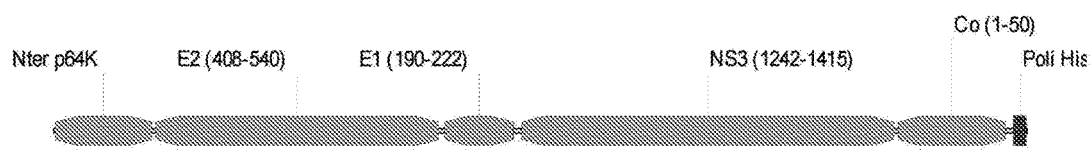
Figure 2:
Figure 2:
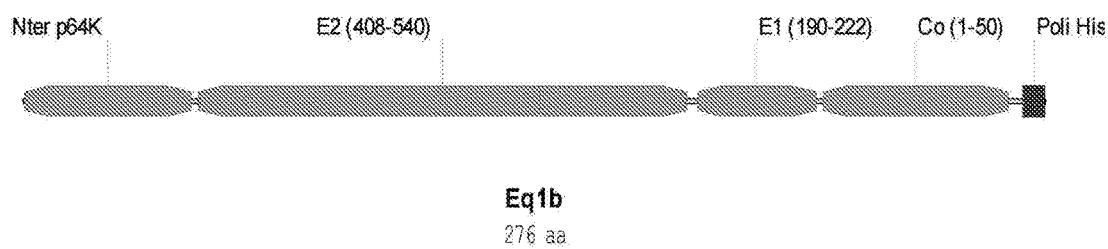

As shown in FIG. 2, the chimeric antigen Coq1 (SEQ ID No. 9) comprises the regions Core (amino acids 1-50), E1 (amino acids 190-222) and E2 (amino acids 408-540) of the HCV polyprotein, located in this particular order. The chimeric antigen Eq1 (SEQ ID No. 10) comprises, equally, the regions E2 (amino acids 408-540, E1 (amino acids 190-222) and Core (amino acids 1-50) of the HCV polyprotein, but in this other particular order. The chimeric antigen E1q1 (SEQ ID No. 11) comprises the same regions but in the following order: E1 (amino acids 190-222), E2 (amino acids 408-540, and Core (amino acids 1-50) of HCV polyprotein. The chimeric antigen NSEq2 (SEQ ID No. 12) includes the epitopes P2B and P1M, in this order, inserted in Eq1, between E1 (amino acids 190-222) and Core (amino acids 1-50) regions. On the other hand, the chimeric antigen EqNSb (SEQ ID No. 13) includes the epitope P2B inserted in Eq1 between E1 (amino acids 190-222) and Core (amino acids 1-50) regions. The chimeric antigen EqNS3 (SEQ ID No. 14) includes the region of amino acids 1242-1415 of HCV polyprotein, inserted between E1 (amino acids 190-222) and Core (amino acids 1-50) regions of the chimeric antigen Eq1. The chimeric antigen EqP1 (SEQ ID No. 15) includes the epitope P1M inserted in Eq1, between E1 (amino acids 190-222) and Core (amino acids 1-50) regions. The chimeric antigen Eq1b (SEQ ID No. 16) comprises the regions E2 (amino acids 408-540), E1 (amino acids 190-222) and Core (amino acids 1-50) of HCV polyprotein, in this particular order, but in this case the amino acids sequence corresponds to the HCV strain H77, genotype 1a (NCBI Reference Sequence: NC_004102.1).

The artificial epitopes P1M and P2B, included in some of the chimeric antigens were designed by bioinformatics to be recognized by human T helper lymphocytes. The binding motifs to HLA-DR13 and HLA-DR11 were studied, using the programs Rankpep, SYFPETHI and ProPred, in order to propose the amino acids variants per position in the artificial epitopes, according to the frequency of appearance. As artificial epitopes specific for T helper lymphocytes are described P1M, of 14 amino acids, which sequence is LPEYVIMVKLPSRA (SEQ ID No. 17); and P2B, of 15 amino acids, which sequence is GYKVIVLNPRVASTL (SEQ ID No. 18).

For the expression of the recombinant protein antigens, competent cells of the bacterial strain *E. coli* GC-366 were transformed with the respective plasmids. The expression of the recombinant proteins was developed during 12 h at 37 degrees Celsius, employing minimal cell culture medium. All protein antigens comprised for protein expression, at the N-terminus, a fragment coming from P64K protein from *Neisseria meningitidis*, previously known for this function (Yero D y cols., Biotechnol Appl Biochem. 2006; 44 (Pt 1):27-34). On the other hand, the protein variants comprise at the C-terminus a six-hystidine tag with the objective to facilitate protein purification. In fact, proteins were purified through solubilization of insoluble fraction coming from cell disruption, with carbonate-bicarbonate pH 9.6 buffer, Urea 8M, and posterior metal chelating affinity chromatography.

Example 2. Immunogenicity Study in Mice of Different Chimeric Antigens Comprising HCV Epitopes Female BALB/c mice, 8 weeks old, 16-18 g of weight, 17 animals per group, were immunized. The immunization groups were as follows: Group 1, chimeric antigen Coq1 formulated in Alum; Group 2, antigen E1q1 formulated in Alum; Group 3, antigen Eq1 formulated in Alum; Group 4, Alum (control group). In all cases, 20 μg of recombinant antigens were administered. The immunizations were carried out at weeks 0, 2 and 4, by intramuscular injection.

Blood collection was carried out at weeks 0 and 6 to study the antibody response against HCV antigens. Moreover, 5 mice per group were sacrificed at week 6 to study specific cellular response. Additionally, 5 animals per group were challenged with the recombinant vaccinia virus vvRE (Alvarez-Lajonchere y cols., Biotecnología Aplicada 2007; 24 (3-4): 246-253), expressing HCV structural proteins and other 5 animals with the control vaccinia virus WR, at week 6. Five days after challenge, mice were sacrificed and the viral titer was determined in ovaries, as previously described (Alvarez-Lajonchere y cols., Biotechnol Appl Biochem. 2008; 51 (Pt 2):97-105).

Figure 3:
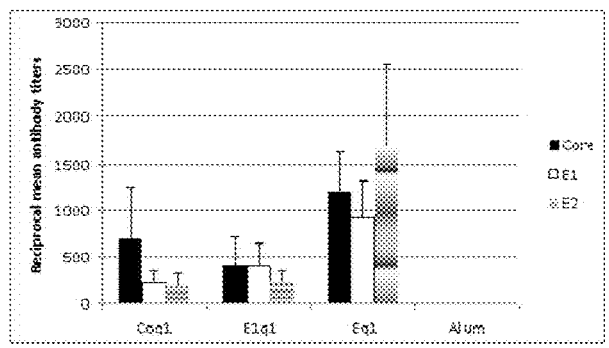
FIG. 3. Antibody response against HCV proteins in the immunization schedules with different chimeric antigens. Results are shown on the Y axis as the reciprocal of the antibody titer, defined as the maximum dilution at which sera show an optical density at 492 nm at least two times higher than the mean optical density of the negative control group sera, determined by ELISA. On the X axis, the different immunogens administered to BALB/c mice are shown. Error bars show the standard deviation of the mean values of each group. The immune response was assessed using recombinant variants of Core (amino acids 1-120 of the capsid protein), E1 (amino acids 192-340 of HCV polyprotein) and E2 (amino acids 384-680 of HCV polyprotein) as coating antigens on the ELISA.
Figure 4:
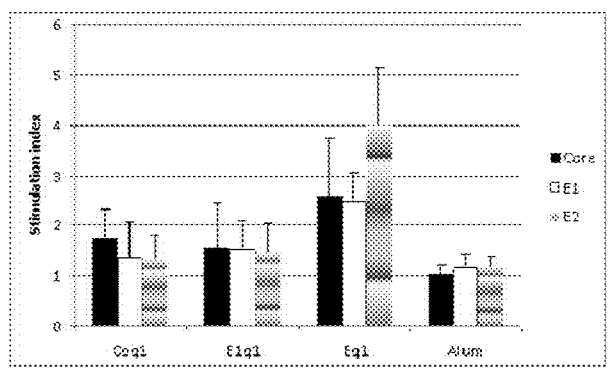
FIG. 4. Proliferative response against HCV proteins in the immunization schedule with different chimeric antigens. Results are shown on the Y axis as the stimulation index, defined as the ratio of cells proliferating on stimulation to cells proliferating without stimulation, determined in a cytometry assay with CFSE staining. A stimulation index greater than two is considered positive. On the X axis, the different immunogens administered to BALB/c mice are shown. Error bars show the standard deviation of the mean values of each group. The immune response was assessed using recombinant variants of Core (amino acids 1-120 of the capsid protein), E1 (amino acids 192-340 of HCV polyprotein) and E2 (amino acids 384-680 of HCV polyprotein) as cell-stimulating antigens.
Figure 5:
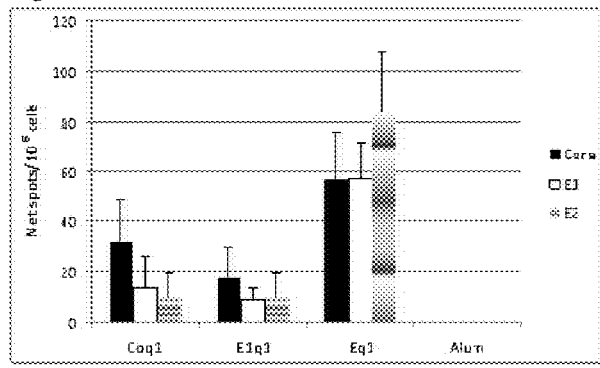
FIG. 5. Response of IFN gamma secretion against HCV proteins in the immunization schedule with different chimeric antigens. Y axis represents the number of net spots per million of cells, which is defined as the number of detected spots on the stimulated condition minus the number of detected spots on the unstimulated condition, determined by IFN gamma secretion ELISPOT assay. On the X axis, the different immunogens administered to BALB/c mice are shown. Error bars show the standard deviation of the mean values of each group. The immune response was assessed using recombinant variants of Core (amino acids 1-120 of the capsid protein), E1 (amino acids 192-340 of HCV polyprotein) and E2 (amino acids 384-680 of HCV polyprotein) as cell-stimulating antigens.
Figure 6:
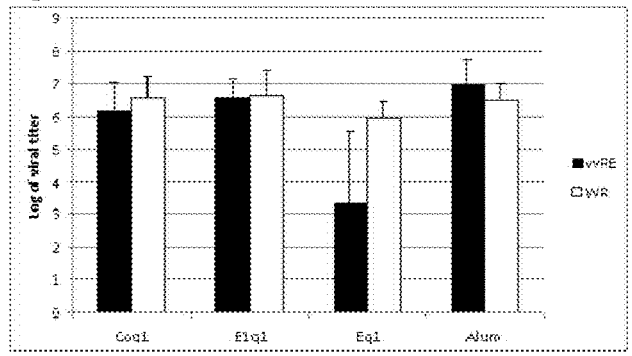
FIG. 6: Response against viral challenge in the immunization schedule with different chimeric antigens. The results are shown in the Y axis as the logarithm of the viral titer, defined as the logarithm of the number of plaque forming units per mL, detected in the ovaries of female mice after the viral challenge. The vaccinia viruses used for the viral challenge were vvRE virus, vaccinia virus expressing Core, E1 and E2 antigens (1-650 amino acid region in the HCV polyprotein) and WR vaccinia virus which does not express HCV antigens. The X axis shows the different immunogens administered to BALB/c mice. Error bars show the standard deviation of the mean values of each group.

The specific immune response against HCV antigens is shown in FIGS. 3 to 5. The evaluated response was detected employing recombinant variants of Core protein (amino acids 1-120, Alvarez-Obregon J C y cols. Vaccine 2001; 19: 3940-3946), E1 (amino acids 192-340 of HCV polyprotein, Lorenzo L J y cols., Biotechnol Appl Biochem 2000; 32(2): 137-143), and E2 (amino acids 384-680 of HCV polyprotein, Martinez-Donato y cols., Mol Biotechnol. 2007; 35(3): 225-36) as capture antigens in ELISA, or as antigens for the stimulation in the assays for determining cellular immune response. As shown in FIG. 3, the antibody response against HCV structural proteins was higher in the group immunized with Eq1 ($p<0.0001$; Kruskal Wallis and Dunns multiple comparison tests), against all the evaluated antigens. A similar behavior was observed for the proliferative response (FIG. 4) and for IFN gamma secretion (FIG. 5), respectively. Additionally, as shown in FIG. 6, the group immunized with protein Eq1 was the only one able to significantly control the specific viremia (after challenge with vvRE), in the surrogate challenge model ($p=0.0069$, Kruskal Wallis and Dunns multiple comparisons tests).

These results evidenced the capacity of chimeric antigen Eq1 to induce a specific immune response, both humoral and cellular, against several HCV antigens, with functional activity in vivo, since it is able to elicit protection in a surrogate challenge model. Additionally, it is evidenced that the order in which the selected regions of HCV structural proteins are located in the chimeric antigens is critical for the induction of specific immune response, and for the development of a functionally protective immune response in a challenge model, since the variants Coq1 and E1q1 failed to induce this type of immune response. Therefore, it is not enough having the epitopes in the antigen but having them in the right context.

Example 3. Immunogenicity Study in Mice of Eq1 Antigen Mixed with NS3

Female BALB/c mice, 8 weeks old, 16-18 g of weight, 17 animals per group were immunized. The immunization groups were as follows: Group 1, antigen Eq1 formulated in Alum; Group 2, antigen Eq1 mixed with the recombinant protein NS3 (Palenzuela D et al., Biotecnología Aplicada 2006; 23: 94-98) formulated in Alum; Group 3, recombinant protein NS3, formulated in Alum; Group 4, Alum (control group). In all cases, 20 μg of recombinant antigen Eq1 and 10 μg of NS3 protein were administered in the corresponding groups. The immunizations were carried out at weeks 0, 2 and 4, by intramuscular injection.

Blood collection was carried out at weeks 0 and 6 to study the antibody response against HCV antigens. Moreover, 5 mice per group were sacrificed at week 6 to study specific cellular response. Additionally, 5 animals per group were challenged with the recombinant vaccinia virus vvRE (Alvarez-Lajonchere y cols., Biotecnología Aplicada 2007; 24 (3-4): 246-253), expressing HCV structural proteins and other 5 animals with the control vaccinia virus WR, at week 6. Five days after challenge, mice were sacrificed and the viral titer was determined in ovaries, as previously described.

Figure 7:
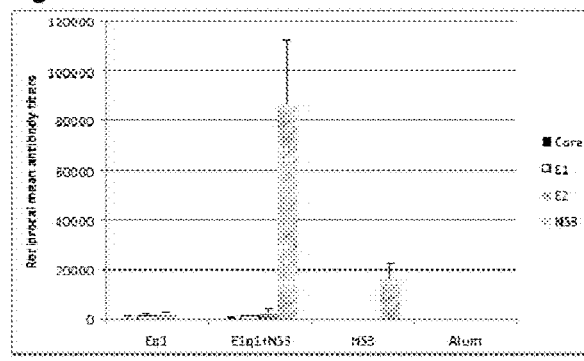
FIG. 7: Antibody response against HCV proteins in the immunization schedule with Eq1 mixed with NS3. The results are shown in the Y axis as the reciprocal antibody titer determined by ELISA. The X axis shows the different immunogens administered to BALB/c mice. Error bars show the standard deviation of the mean values of each group. The response was evaluated using recombinant variants of the Core protein (amino acids 1-120 of the capsid protein), E1 (amino acids 192-340 of the HCV polyprotein), E2 (amino acids 384-680 of the HCV polyprotein) and NS3 (amino acids 1192-1457 of the HCV polyprotein) as coating antigens in the ELISA.
Figure 8:
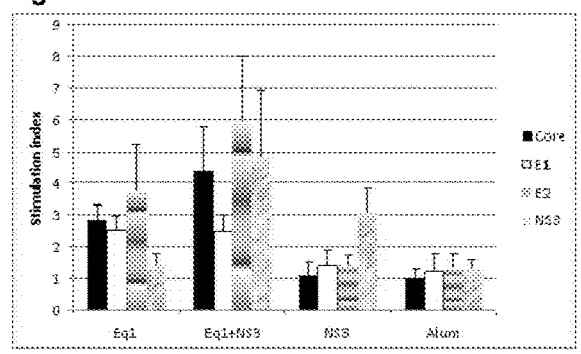
FIG. 8: Proliferative response against HCV proteins in the immunization schedule with Eq1 mixed with NS3. The results are shown in the Y axis as the stimulation index, determined in a cytometry assay with CFSE staining. A stimulation index greater than two is considered positive. The X axis shows the different immunogens administered to BALB/c mice. Error bars show the standard deviation of the mean values of each group. The response was evaluated using recombinant variants of the Core protein (amino acids 1-120 of the capsid protein), E1 (amino acids 192-340 of the HCV polyprotein) and NS3 (amino acids 1192-1457 of the HCV polyprotein) as cell-stimulating antigens.
Figure 9:
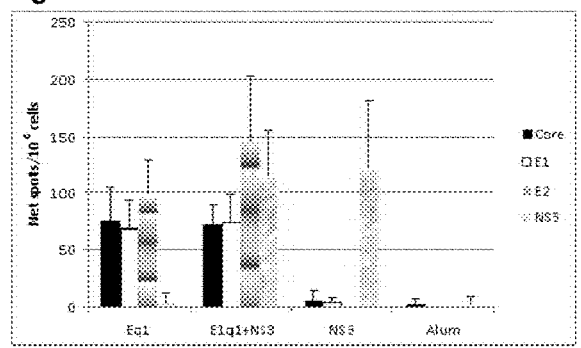
FIG. 9: Response of IFN gamma secretion against HCV proteins in the immunization schedule with Eq1 mixed with NS3. Y axis represents the number of net spots per million of cells determined by IFN gamma secretion ELISPOT assay. The X axis shows the different immunogens administered to BALB/c mice. Error bars show the standard deviation of the mean values of each group. The response was evaluated using recombinant variants of the Core Protein (amino acids 1-120 of the capsid protein), E1 (amino acids 384-680 of the HCV polyprotein) and NS3 (amino acids 1192-1457 of the HCV polyprotein) as cell-stimulating antigens.

The specific immune response against HCV antigens is shown in FIGS. 7 to 9. The evaluated immune response was detected employing recombinant variants of Core protein (amino acids 1-120), E1 (amino acids 192-340 of HCV polyprotein), E2 (amino acids 384-680 of HCV polyprotein), and NS3 (amino acids 1192-1457 in HCV polyprotein), as capture antigens in ELISA, or as antigens for the stimulation in the assays for determining cellular immune response. As shown in FIG. 7, antibody response is induced against HCV structural antigens in the groups immunized with Eq1 individually or mixed with NS3, without statistically significant differences among them. However, the antibody response against NS3 was significantly superior in the group of the mixture of NS3 and Eq1 ($p=0.0001$, Mann Whitney test).

On the other hand, the analysis of the proliferative response, represented in FIG. 8, evidenced a response significantly superior against Core, E2 and NS3 antigens, in the group administered with the mixture of Eq1 with NS3, with respect to the administration of the individual antigens ($p<0.05$, ANOVA and Newman-Keuls multiple comparisons tests). Statistically significant differences between the groups immunized with Eq1 individually or mixed with NS3 were not observed with respect to the response against E1.

Figure 10:
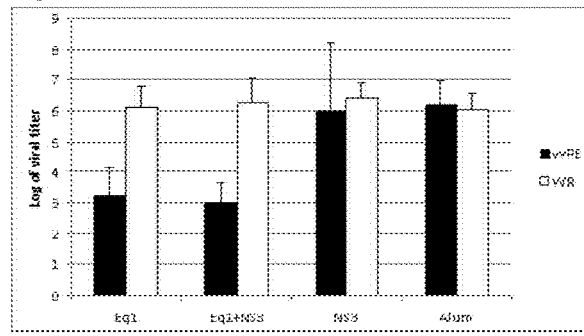
FIG. 10: Response against viral challenge in the immunization schedule with Eq1 mixed with NS3. The results are shown in the Y axis as the logarithm of the viral titer. The vaccinia viruses used for the viral challenge were vvRE and WR. The X axis shows the different immunogens administered to BALB/c mice. Error bars show the standard deviation of the mean values of each group.

Regarding the specific IFN gamma secretion response, that is represented in FIG. 9, it was induced with statistically significant differences among the variants immunized with the recombinant proteins, only with respect to the E2 antigen, which shows a significantly superior response in the group immunized with the mixture of Eq1 and NS3 ($p<0.05$, ANOVA and Newman-Keuls multiple comparison tests). Additionally, as shown in FIG. 10, both the group immunized with the Eq1 protein individually or mixed with NS3 significantly controlled the specific viremia (challenge with vvRE), in the surrogate challenge model ($p<0.05$, Kruskal Wallis and Dunns multiple comparisons tests).

These results evidenced that the preparation based in the mixture of antigen Eq1 with NS3 is able to induce an increased specific immune response, both humoral and cellular, against HCV structural antigens and NS3, with functional activity in vivo, since it is capable of providing protection in a surrogate viral challenge model.

Example 4. Immunogenicity Study in Mice of the Chimeric Antigen Eq1 Mixed with a Plasmid for DNA Immunization Female BALB/c mice, 8 weeks old, 16-18 g of weight, 17 animals per group were immunized. The immunization groups were as follows: Group 1, Eq1 antigen formulated in Alum; Group 2, Eq1 antigen mixed with the plasmid for DNA immunization pIDKE2 (Dueñas-Carrera y cols., Biotechnol Appl Biochem. 2004; 39: 249-55) in saline solution; Group 3, Eq1 antigen mixed with pIDKE2 plasmid and with Co. 120 protein (Dueñas-Carrera y cols., Biotecnología Aplicada 1999; 16(4), 226-231) in saline solution; Group 4, Co. 120 protein mixed with pIDKE2 plasmid in saline solution, at weeks 0 and 3, with a dose of Eq1 antigen formulated in Alum at week 6; Group 5, pIDKE2 plasmid in saline solution at weeks 0, 3 and 6; Group 6, Alum (control); Group 7, saline solution (control). Mice received 20 µg of chimeric Eq1 antigen and 10 µg of Co. 120 recombinant protein in the corresponding groups. In the case of pIDKE2 plasmid, 100 µg were administered in each dose. The immunizations were carried out at weeks 0, 3 and 6 by intramuscular injection.

Blood collection was carried out at weeks 0 and 8 to study the antibody response against HCV antigens. Moreover, 5 mice per group were sacrificed at week 8 for studying specific cellular response. Additionally, 5 animals per group were challenged with the recombinant vaccinia virus vvRE, expressing HCV structural proteins, and other 5 animals with the control vaccinia virus WR, at week 8. Five days after challenge, the mice were sacrificed and the viral titers were determined in ovaries, as previously described.

Figure 11:
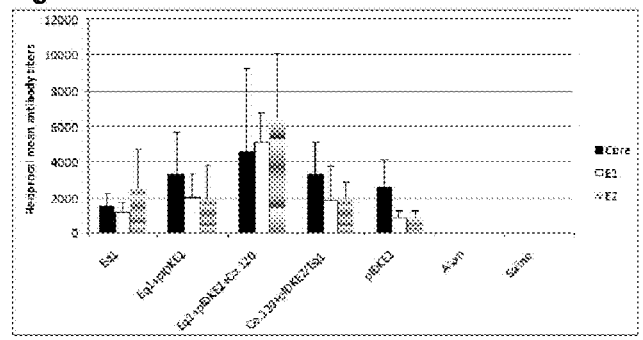
FIG. 11: Antibody response against HCV proteins in the immunization schedule with Eq1 combined with plasmid for DNA immunization. The results are shown in the Y axis as the reciprocal antibody titer determined by ELISA. The X axis shows the different immunogens administered to BALB/c mice. Error bars show the standard deviation of the mean values of each group. The response was evaluated using recombinant variants of the Core protein (amino acids 1-120 of the capsid protein), E1 (amino acids 192-340 of the HCV polyprotein) and E2 (amino acids 384-680 of the HCV polyprotein) as coating antigens in the ELISA.
Figure 12:
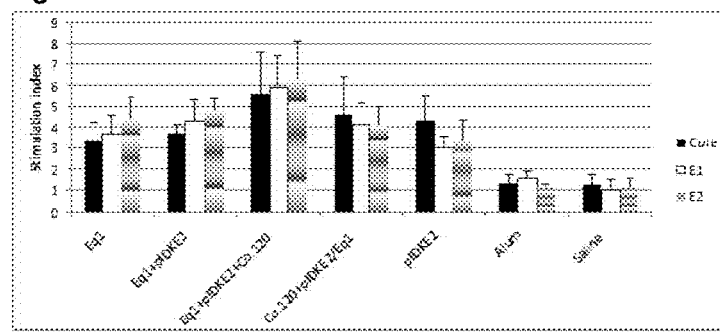
FIG. 12: Proliferative response against HCV proteins in the immunization schedule with Eq1 combined with plasmid for DNA immunization. The results are shown in the Y axis as the stimulation index, determined in a cytometry assay with CFSE staining. A stimulation index greater than two is considered positive. The X axis shows the different immunogens administered to BALB/c mice. Error bars show the standard deviation of the mean values of each group. The immune response was assessed using recombinant variants of Core (amino acids 1-120 of the capsid protein), E1 (amino acids 192-340 of HCV polyprotein) and E2 (amino acids 384-680 of HCV polyprotein) as cell-stimulating antigens.
Figure 13:
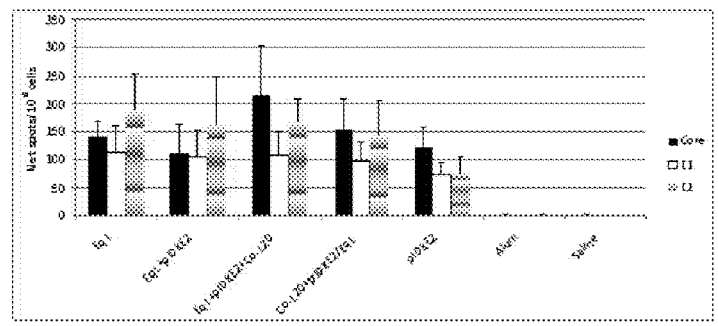
FIG. 13: Response of IFN gamma secretion against HCV proteins in the immunization schedule with Eq1 combined with plasmid for DNA immunization. Y axis represents the number of net spots per million of cells, determined by IFN gamma secretion ELISPOT assay. The X axis shows the different immunogens administered to BALB/c mice. Error bars show the standard deviation of the mean values of each group. The response was evaluated using recombinant variants of the Core protein (amino acids 1-120 of the capsid protein), E1 (amino acids 192-340 of the HCV polyprotein) and E2 (amino acids 384-680 of the HCV polyprotein) as cell-stimulating antigens.

The specific immune response against HCV antigens is shown in FIGS. 11 to 13. The evaluated response was detected employing recombinant variants of Core protein (amino acids 1-120), E1 (amino acids 192-340 of HCV polyprotein), and E2 (amino acids 384-680 of HCV polyprotein) as capture antigens in ELISA, or as antigens for the stimulation in the assays for determining cellular immune response. As shown in FIG. 11, an antibody response against HCV structural antigens is induced in all immunized groups, with the exception of the controls. A significantly higher antibody response against E1 and E2 was detected in the group immunized with the mixture of Eq1 protein and Co. 120 with pIDKE2 plasmid, with respect to the group immunized with pIDKE2 plasmid alone (p<0.05, Kruskal Wallis and Dunns multiple comparison tests). Equally, statistically significant differences between these two groups were observed with respect to the proliferative response (FIG. 12), against Core, E1 and E2 (p<0.05, Kruskal Wallis and Dunns multiple comparison tests). In fact, the group immunized with the mixture of Eq1 protein and Co. 120 with pIDKE2 plasmid induced a proliferative response against E1 and E2 antigens, which was significantly superior to that induced in the remaining groups (p<0.05, ANOVA and Newman-Keuls multiple comparisons tests), with the exception of the group immunized in the prime/boost schedule (Group 4).

Regarding the IFN gamma secretion response, all the groups induced a detectable response (FIG. 13) against HCV structural proteins (with the exception of controls). Statistically significant differences in the responses against E1 and E2 were not observed among the groups vaccinated with the immunogenic variants, with the exception of the observed superiority (p<0.05, ANOVA and Newman-Keuls multiple comparisons tests) in the response induced against E2, in the group immunized with Eq1 individually (Group 1) with respect to the group immunized with pIDKE2 plasmid alone (Group 5). However, the IFN gamma secretion response against the Core antigen was significantly superior in the group immunized with the mixture of Eq1 and Co. 120 proteins with pIDKE2 plasmid, with respect to the remaining groups (p<0.05; ANOVA and Newman-Keuls multiple comparisons tests), with the exception of the group immunized in the prime/boost schedule (Group 4).

Figure 14:
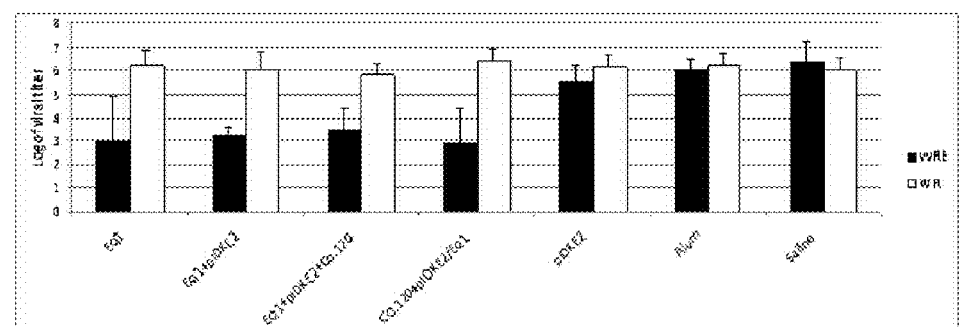
FIG. 14: Response against viral challenge in the immunization schedule with Eq1 combined with plasmid for DNA immunization. The results are shown in the Y axis as the logarithm of the viral titer detected in ovaries of female mice after the viral challenge. For the viral challenge vvRE and WR viruses were used. The X axis shows the different immunogens administered to BALB/c mice. Error bars show the standard deviation of the mean values of each group.

Additionally, all groups involving the administration of chimeric Eq1 antigen (Groups 1 to 4) were able to significantly control the specific viremia (challenge with vvRE) in the surrogate challenge model (FIG. 14) (p<0.05, Kruskal Wallis and Dunns multiple comparisons tests), but not the remaining groups.

The results evidenced that a vaccine composition based on the administration of Eq1 mixed with pIDKE2 plasmid and Co. 120 protein, or in prime/boost schedules, allows the induction of an increased specific immune response, both humoral and cellular, against HCV structural antigens, with functional activity in vivo, since it is able to induce protection in a surrogate challenge model.

Example 5. Immunogenicity Study in Mice of the Chimeric Antigen Eq1 Mixed with Recombinant Protein Variants of HCV Structural Proteins Female BALB/c mice, 8 weeks old, 16-18 g of weight, 17 animals per group were immunized. The immunization groups were as follows: Group 1, Eq1 antigen formulated in Alum; Group 2, mixtures of Co. 120, E1.340 (Lorenzo L J y cols., Biotechnol Appl Biochem 2000; 32(2):137-143) and E2.680 (Martinez-Donato y cols., Mol Biotechnol. 2007; 35(3): 225-36) proteins, formulated in Alum at week 0 and 2, with doses of chimeric Eq1 antigen formulated in Alum at week 4; Group 3, chimeric Eq1 antigen formulated in Alum at week 0, and doses of the mixture of proteins Co. 120, E1.340 and E2.680, formulated in Alum, at weeks 2 and 4; Group 4, mixture of proteins Co. 120, E1.340, E2.680 and Eq1, formulated in Alum; Group 5, mixture of proteins Co. 120, E1.340 and E2.680, formulated in Alum; Group 6, Alum (control). Mice received 20 µg of chimeric Eq1 antigen; 16.7 µg of E1 and E2 proteins, as well as 0.1 µg of Co. 120 protein, in the corresponding groups. The immunizations were carried out at weeks 0, 2 and 4 by intramuscular injection.

Blood collection was carried out at weeks 0 and 6 to study the antibody response against HCV antigens. Moreover, 5 mice per group were sacrificed at week 6 for studying specific cellular response. Additionally, 5 animals per group were challenged with the recombinant vaccinia virus vvRE, expressing HCV structural proteins, and other 5 animals with the control vaccinia virus WR, at week 8. Five days after challenge, the mice were sacrificed and the viral titers were determined in ovaries, as previously described.

Figure 15:
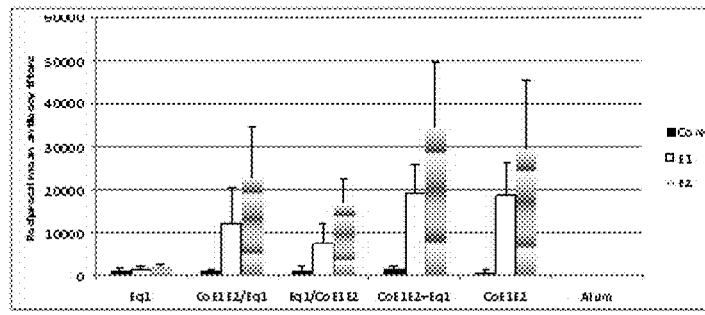
FIG. 15: Antibody response against HCV proteins in the immunization schedule with Eq1 mixed with recombinant variants of the HCV structural proteins. The results are shown in the Y axis as the reciprocal antibody titer determined by ELISA. The X axis shows the different immunogens administered to BALB/c mice. Error bars show the standard deviation of the mean values of each group. The response was evaluated using recombinant variants of the Core protein (amino acids 1-120 of the capsid protein), E1 (192-340 of the HCV polyprotein) and E2 (amino acids 384-680 of the HCV polyprotein) as coating antigens in the ELISA.
Figure 16:
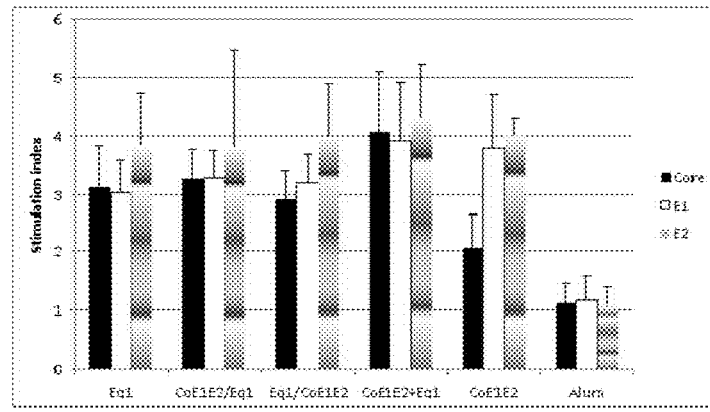
FIG. 16. Proliferative response against HCV proteins in the immunization schedule with Eq1 mixed with recombinant variants of HCV structural proteins. The results are shown as stimulation index, determined in a cytometry assay with CFSE staining. A stimulation index greater than two is considered positive. The different immunogens administered to BALB/c mice are shown. Error bars show the standard deviation of the mean values of each group. The immune response was assessed using recombinant variants of Core (amino acids 1-120 of the capsid protein), E1 (amino acids 192-340 of HCV polyprotein) and E2 (amino acids 384-680 of HCV polyprotein) as cell-stimulating antigens.
Figure 17:
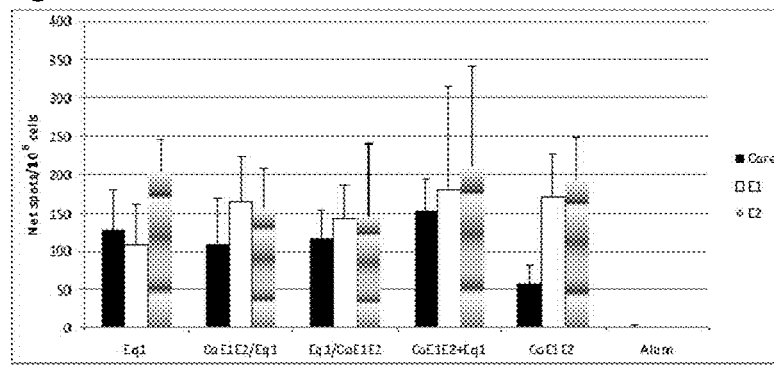
FIG. 17. Response of IFN gamma secretion against HCV proteins in the immunization schedule with Eq1 mixed with recombinant variants of HCV structural proteins. The results are shown as net spots per million cells determined in an IFN-gamma ELISPOT assay. The different immunogens administered to BALB/c mice are shown. Error bars show the standard deviation of the mean values of each group. The immune response was assessed using recombinant variants of Core (amino acids 1-120 of the capsid protein), E1 (amino acids 192-340 of HCV polyprotein) and E2 (amino acids 384-680 of HCV polyprotein) as cell-stimulating antigens.

The specific immune response against HCV is shown in the FIGS. 15 to 17. The evaluated response was detected using recombinant variants of Core protein (amino acids 1-120), E1 (amino acids 192-340 of HCV polyprotein) and E2 (amino acids 384-680 of HCV polyprotein), as capture antigens in ELISA, or as antigens for the stimulation in the assays for determining cellular immune response. As observed in FIG. 15, all immunized groups, with the exception of controls, induced specific antibody response against HCV structural antigens. No statistically significant differences were observed with respect to the antibody response against the Core protein among the groups. In contrast, groups immunized with the mixture of structural proteins (Group 5) and the group immunized with the mixture of structural proteins plus Eq1 (Group 4) had a significantly higher antibody response against E1 and E2 than the group immunized with Eq1 individually (p<0.05, Kruskal Wallis and Dunn's multiple comparison tests).

On the other hand, proliferative response against HCV antigens was induced in all groups, with the exception of the control, as observed in FIG. 16. No statistically significant differences among the groups were observed with respect to the proliferative response against E1 and E2. However, all groups receiving the chimeric Eq1 antigen, in any of the combinations (Groups 1 to 4), induced a proliferative response against Core significantly superior to the induced by the mixture of HCV structural proteins (Group 5) ($p<0.05$, ANOVA and Newman-Keuls multiple comparisons tests).

As shown in FIG. 17, the IFN gamma secretion response had a similar behavior to that observed for the proliferative response. In this case, the group immunized with the mixture of HCV structural proteins (group 5) had an IFN gamma secretion response against Core significantly lower than the induced in the groups immunized with the chimeric Eq1 antigen individually (Group 1) and the mixture of Eq1 with the HCV structural proteins (Group 4) ($p<0.05$, ANOVA and Newman-Keuls multiple comparisons tests).

Figure 18:
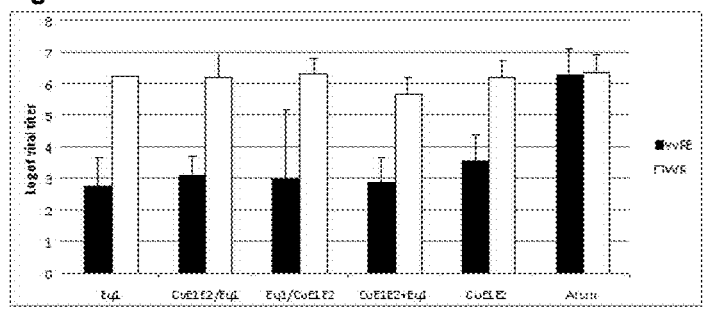
FIG. 18. Response against viral challenge in the immunization schedule with Eq1 mixed with recombinant variants of HCV structural proteins. The results are shown as the logarithm of viral titer detected in the ovaries of female mice after the viral challenge. Vaccinia viruses vvRE and WR were used for viral challenge. The different immunogens administered to BALB/c mice are shown. Error bars show the standard deviation of the mean values of each group.

Additionally, all the groups, with the exception of the control, were able to significantly control the specific viremia (challenge with vvRE) in the viral surrogate challenge model (FIG. 18) ($p<0.05$, Kruskal Wallis and Dunn's multiple comparisons tests). The results evidenced that a vaccine composition based on the administration of the chimeric Eq1 antigen mixed with a preparation comprising recombinant protein variants of HCV structural antigens Core, E1 and E2, allows the induction of increased specific immune response, both humoral and cellular against HCV structural proteins, with functional activity in vivo, since is able to provide protection in the viral surrogate challenge model.

Example 6. Immunogenicity Study in Mice of Different Chimeric Antigens Comprising HCV Epitopes and Artificial Epitopes Specific for T Helper Lymphocytes Female BALB/c mice, 8 weeks old, 16-18 g of weight, 17 animals per group were immunized. The immunization groups were as follows: Group 1, chimeric Eq1 antigen formulated in Alum; Group 2, chimeric NSEq2 antigen formulated in Alum; Group 3, chimeric EqNSb antigen formulated in Alum; Group 4, chimeric EqNS3 antigen formulated in alum; Group 5, chimeric EqP1 antigen formulated in Alum; Group 6, Alum (control). Mice received 20 μg of the recombinant chimeric antigens, in the corresponding groups. The immunizations were carried out at weeks 0, 2 and 4, by intramuscular injection.

Blood collection was carried out at weeks 0 and 6 to study the antibody response against HCV antigens. Moreover, 5 mice per group were sacrificed at week 6 for studying specific cellular response. Additionally, 5 animals per group were challenged with the recombinant vaccinia virus vvRE, expressing HCV structural proteins, and other 5 animals with the control vaccinia virus WR, at week 8. Five days after challenge, the mice were sacrificed and the viral titers were determined in ovaries, as previously described.

Figure 19:
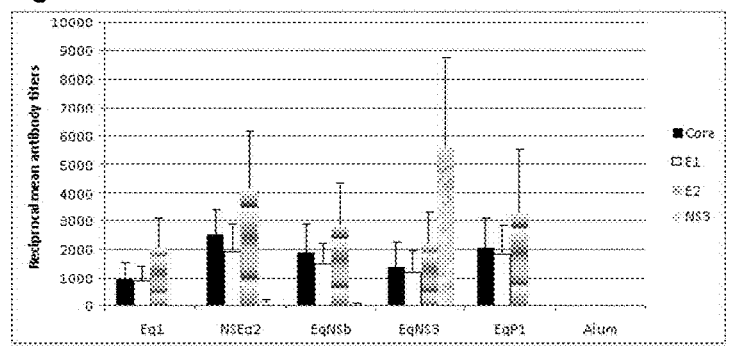
FIG. 19. Antibody response against HCV proteins in the immunization schedule with different chimeric antigens that include artificial epitopes and epitopes of the NS3 protein. The results are shown as the reciprocal mean antibody titer, determined by ELISA. The different immunogens administered to BALB/c mice are shown. Error bars show the standard deviation of the mean values of each group. The immune response was assessed using recombinant variants of Core (amino acids 1-120 of the capsid protein), E1 (amino acids 192-340 of HCV polyprotein) and E2 (amino acids 384-680 of HCV polyprotein) and NS3 (amino acids 1192-1457 of HCV polyprotein) as coating antigens on the ELISA.
Figure 20:
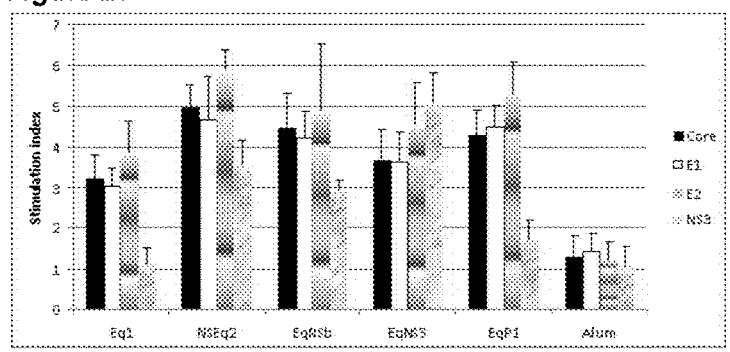
FIG. 20. Proliferative response against HCV proteins in the immunization schedule with different chimeric antigens that include artificial epitopes and epitopes of the NS3 protein. The results are shown as stimulation index, determined in a cytometry assay with CFSE staining. A stimulation index greater than two is considered positive. The different immunogens administered to BALB/c mice are shown. Error bars show the standard deviation of the mean values of each group. The immune response was assessed using recombinant variants of Core (amino acids 1-120 of the capsid protein), E1 (amino acids 192-340 of HCV polyprotein) and E2 (amino acids 384-680 of HCV polyprotein) and NS3 (amino acids 1192-1457 of HCV polyprotein) as cell-stimulating antigens.
Figure 21:
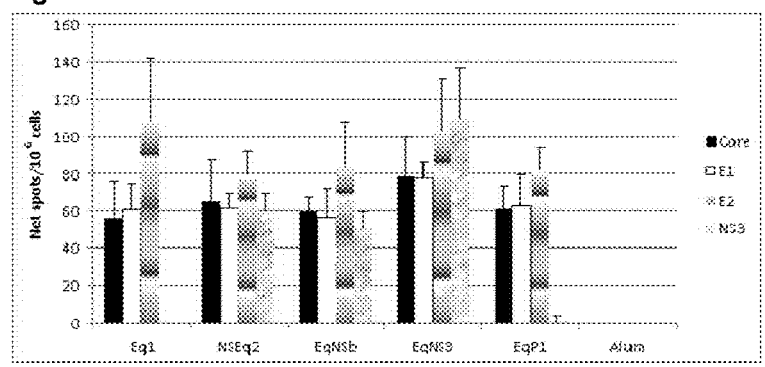
FIG. 21. Response of IFN gamma secretion against HCV proteins in the immunization schedule with different chimeric antigens that include artificial epitopes and epitopes of the NS3 protein. The results are shown as net spots per million cells determined in an IFN-gamma ELISPOT assay. The different immunogens administered to BALB/c mice are shown. Error bars show the standard deviation of the mean values of each group. The immune response was assessed using recombinant variants of Core (amino acids 1-120 of the capsid protein), E1 (amino acids 192-340 of HCV polyprotein) and E2 (amino acids 384-680 of HCV polyprotein) and NS3 (amino acids 1192-1457 of HCV polyprotein) as cell-stimulating antigens.

The specific immune response against HCV antigens is shown in FIGS. 19 to 21. The evaluated response was detected employing recombinant variants of Core (amino acids 1-120), E1 (amino acids 192-340 of HCV polyprotein), E2 (amino acids 384-680 of HCV polyprotein) and NS3 (amino acids 1192 to 1457 in the HCV polyprotein) proteins, as capture antigens in ELISA, or as antigens for stimulation in the assays for determining cellular immune response. As shown in FIG. 19, in all the groups, with the exception of the control, a specific antibody response was induced against HCV structural proteins, without statistically significant differences among the groups immunized with the different chimeric antigens. Only the groups 2, 3 and 4, comprising regions of HCV NS3 induced antibody response against this viral antigen, being significantly superior in the Group 4 with respect to the Groups 2 and 3 ($p<0.05$, ANOVA and Newman-Keuls multiple comparison tests).

As shown in FIG. 20, in all groups, with the exception of the control, a specific proliferative response was elicited against HCV structural antigens. In this case, the proliferative response against Core and E1 antigens was significantly higher in the Groups 2, 3 and 5 with respect to Group 1 ($p<0.05$, ANOVA and Newman-Keuls multiple comparisons tests). No statistically significant differences were detected among the groups immunized with the different chimeric antigens with respect to the proliferative response against E2. Only Groups 2, 3 and 4, comprising regions of HCV NS3 elicited proliferative response against this viral antigen, being significantly superior in the Group 4 with respect to the groups 2 and 3 ($p<0.05$, ANOVA and Newman-Keuls multiple comparisons tests).

Figure 22:
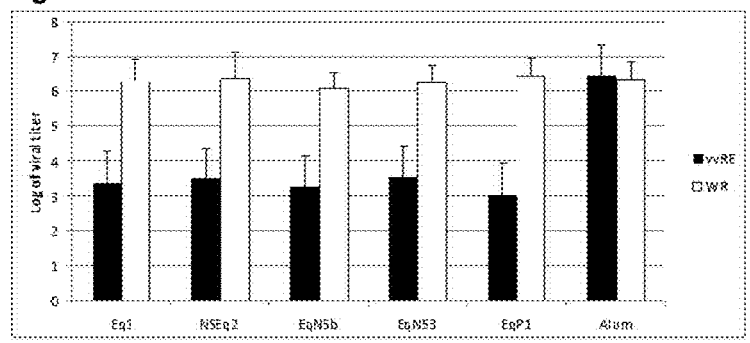
FIG. 22. Response against viral challenge in the immunization schedule with different chimeric antigens that include artificial epitopes and epitopes of the NS3 protein. The results are shown as the logarithm of viral titer detected in the ovaries of female mice after the viral challenge. Vaccinia viruses vvRE and WR were used for viral challenge. The different immunogens administered to BALB/c mice are shown. Error bars show the standard deviation of the mean values of each group.

The analysis of the specific IFN gamma secretion response (FIG. 21), evidenced its induction against HCV structural antigens in all groups, with the exception of the control, without statistically significant differences among them. Only the Groups 2, 3 and 4, comprising regions of HCV NS3, induced IFN gamma secretion response against this viral antigen, without statistically significant differences among them. Additionally, all the groups, with the exception of the control, were able to significantly control the specific viremia (challenge with vvRE) in the viral surrogate challenge model (FIG. 22) ($p<0.05$, Kruskal Wallis and Dunn's multiple comparisons tests). The results evidenced that the insertion of epitopes or regions of HCV NS3 in the sequence of Eq1 allows the induction of specific immune response against this viral antigen without affecting the immune response induced against the HCV structural antigens. Moreover, the inclusion of artificial epitopes P1M and P2B in the sequence of Eq1 protein allows the significant increase of proliferative response against Core and E1 antigens, without affecting the ability to induce specific humoral or cellular immune response against these antigens or E2, and keeping also the functional activity in vivo, since it is able to provide protection in the viral surrogate challenge model.

Example 7. Comparative Immunogenicity Study in Mice of Chimeric Antigens Eq1 and Eq1b Female BALB/c mice, 8 weeks old, 16-18 g of weight, 17 animals per group were immunized. The immunization groups were as follows: Group 1, chimeric Eq1b antigen formulated in Alum; Group 2, chimeric Eq1 antigen formulated in Alum; Group 3, Alum (control). Mice received 20 μg of chimeric antigens, in the corresponding groups. The immunizations were carried out at weeks 0, 2 and 4, by intramuscular injection.

Blood collection was carried out at weeks 0 and 6 to study the antibody response against HCV antigens. Moreover, 5 mice per group were sacrificed at week 6 for studying specific cellular response. Additionally, 5 animals per group were challenged with the recombinant vaccinia virus vvRE, expressing HCV structural proteins, and other 5 animals with the control vaccinia virus WR, at week 8. Five days after challenge, the mice were sacrificed and the viral titers were determined in ovaries, as previously described.

Figure 23:
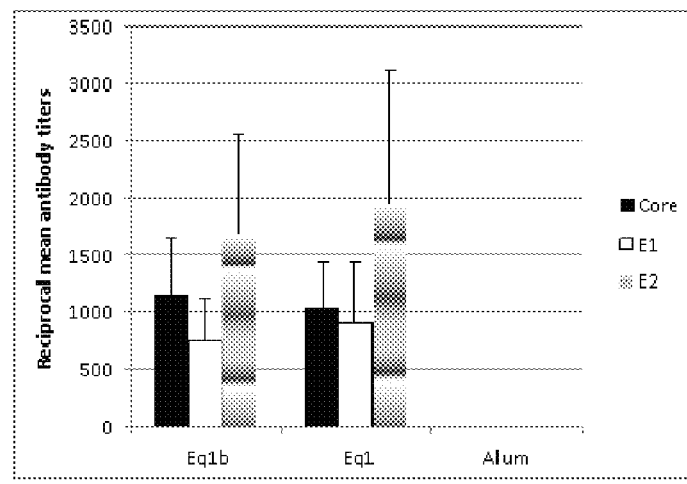
FIG. 23. Antibody response against HCV proteins in the immunization schedule with chimeric antigens Eq1 and Eq1b. The results are shown as the reciprocal mean antibody titer, determined by ELISA. The different immunogens administered to BALB/c mice are shown. Error bars show the standard deviation of the mean values of each group. The immune response was assessed using recombinant variants of Core (amino acids 1-120 of the capsid protein), E1 (amino acids 192-340 of HCV polyprotein) and E2 (amino acids 384-680 of HCV polyprotein) as coating antigens on the ELISA.
Figure 24:
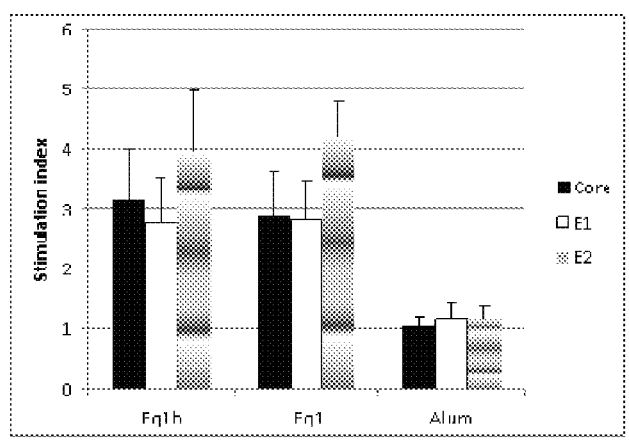
FIG. 24. Proliferative response against HCV proteins in the immunization schedule with chimeric antigens Eq1 and Eq1b. The results are shown as stimulation index, determined in a cytometry assay with CFSE staining. A stimulation index greater than two is considered positive. The different immunogens administered to BALB/c mice are shown. Error bars show the standard deviation of the mean values of each group. The immune response was assessed using recombinant variants of Core (amino acids 1-120 of the capsid protein), E1 (amino acids 192-340 of HCV polyprotein) and E2 (amino acids 384-680 of HCV polyprotein) as cell-stimulating antigens.

The specific immune response against HCV antigens is shown in FIGS. 23 and 24. The evaluated response was detected employing recombinant variants of Core (amino acids 1-120), E1 (amino acids 192-340 of HCV polyprotein) and E2 (amino acids 384-680 of HCV polyprotein) proteins, as capture antigens in ELISA, or as antigens for the stimulation in the assays for determining cellular immune response. As shown in the above mentioned figures, in the groups immunized with the proteins, but not in the control, specific antibody and proliferative responses against HCV structural antigens were induced, without statistically significant differences between the groups immunized with the recombinant proteins.

Figure 25:
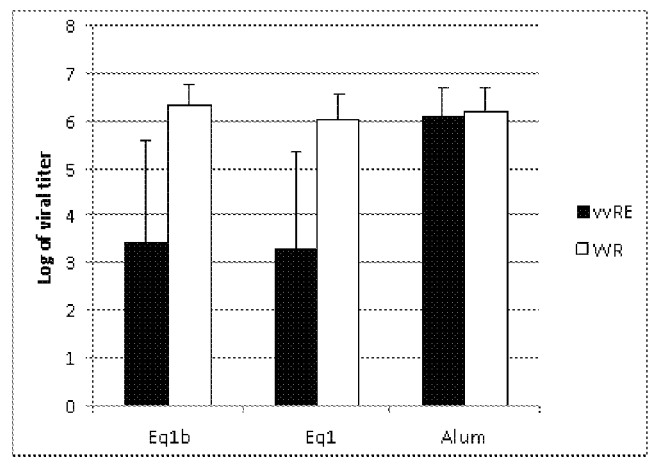
FIG. 25. Response against viral challenge in the immunization schedule with chimeric antigens Eq1 and Eq1b. The results are shown as the logarithm of viral titer detected in the ovaries of female mice after the viral challenge. Vaccinia viruses vvRE and WR were used for viral challenge. The different immunogens administered to BALB/c mice are shown. Error bars show the standard deviation of the mean values of each group.

On the other hand, the groups immunized with the chimeric antigens, but not the control, were able to significantly control the specific viremia (challenge with vvRE) in the viral surrogate challenge model (FIG. 25) ($p<0.05$; Kruskal Wallis and Dunn's multiple comparisons tests), without differences between the groups immunized with the recombinant proteins.

INCORPORATION OF SEQUENCE LISTING

Incorporated herein by reference in its entirety is the Sequence Listing for the application. The Sequence Listing is disclosed on a computer-readable ASCII text file titled, "sequence_listing.txt", created on May 4, 2015. The sequence_listing.txt file is 58.5 kb in size.

The invention claimed is:

1. A chimeric antigen against hepatitis C virus (HCV) comprising
    a) a first segment consisting of the E2 region (amino acids 408-540) of HCV polyprotein,
    b) a second segment consisting of the E1 region (amino acids 190-222) of HCV polyprotein, and
    c) a third segment consisting of the Core region (amino acids 1 to 50) of this protein,
wherein the order of the first to third segments is 5' to 3'.

2. The chimeric antigen of claim 1, wherein its amino acids sequence is selected among the group composed by SEQ ID NO: 10 (Eq1 antigen) and SEQ ID No. 16 (Eq1b antigen).

3. The chimeric antigen of claim 1 characterized by additionally in its sequence comprises at least one epitope specific for T helper lymphocytes.

4. The chimeric antigen of claim 3 wherein the epitope specific for T helper lymphocytes is an epitope of HCV nonstructural proteins.

5. The chimeric antigen of claim 4 wherein the nonstructural protein is NS3.

6. The chimeric antigen of claim 5 characterized by its amino acids sequence is SEQ ID NO: 14 (EqNS3 antigen).

7. The chimeric antigen of claim 3 wherein the epitope specific for T helper lymphocytes is an artificial epitope.

8. The chimeric antigen of claim 7 where the artificial epitope is selected from the group composed by the epitope P1M (SEQ ID NO: 17) and the epitope P2B (SEQ ID NO: 18).

9. The chimeric antigen of claim 8 characterized by its amino acids sequence is selected from the group composed by SEQ ID No. 12 (NSEq2 antigen), SEQ ID No. 13 (EqNSb antigen) and SEQ ID No. 15 (EqP1 antigen).

10. A composition comprising a chimeric vaccine antigen against HCV comprising:
    a) a first segment consisting of the E2 region (amino acids 408-540) of HCV polyprotein,
    b) a second segment consisting of the E1 region (amino acids 190-222) of HCV polyprotein, and
    c) a third segment consisting of the Core region (amino acids 1 to 50) of the HCV polyprotein, wherein the order of the first to third segments is 5' to 3'; and
excipients and/or pharmaceutically acceptable adjuvants.

11. The composition of claim 10 which it additionally comprises a recombinant protein variant of HCV structural antigens or the HCV NS3 antigen.

12. The composition of claim 10 which additionally comprises a plasmid for DNA immunization expressing the HCV structural antigens.

13. The composition of claim 10 which additionally comprises a plasmid for DNA immunization expressing the HCV structural antigens, and a recombinant capsid protein of HCV.

14. The composition of claim 10 which can be administered in prime/boost schedules with preparations based on plasmids for DNA immunization, recombinant proteins of HCV structural antigens, or a mixture of both.

15. A method for the induction of specific immune response against HCV in a subject in need thereof, the method comprising administering the chimeric antigen of claim 1, or a composition comprising the chimeric vaccine antigen of claim 1, to a subject, wherein the subject is a healthy individual or a patient infected with HCV.

16. The method of claim 15 wherein the chimeric antigen, or the composition, is administered in prime/boost schedules with preparations based on plasmids for DNA immunization, recombinant proteins of HCV structural antigens, or a mixture of both.

* * * * *

SEQUENCE LISTING

```
<160> NUMBER OF SEQ ID NOS: 18

<210> SEQ ID NO 1
<211> LENGTH: 3370
<212> TYPE: DNA
<213> ORGANISM: Artificial Sequence
<220> FEATURE:
<223> OTHER INFORMATION: Artificial Sequence Description: Sequence
      corresponding to pIMCo64K plasmid

<400> SEQUENCE: 1
cgggcacacc atcaccatca ccattaagat ccggtggatg acctttgaa tgacctttaa      60 tagattatat tactaattaa ttggggaccc tagaggtccc tttttattt taaaaatttt     120 ttcacaaaac ggtttacaag cataaagctc tgcattaatg aatcggccaa cgcgcgggga    180
gaggcggttt gcgtattggg cgctcttccg cttcctcgct cactgactcg ctgcgctcgg    240
tcgttcggct gcggcgagcg gtatcagctc actcaaaggc ggtaatacgg ttatccacag    300
aatcagggga taacgcagga aagaacatgt gagcaaaagg ccagcaaaag gccaggaacc    360
gtaaaaaggc cgcgttgctg gcgttttcc ataggctccg ccccctgac gagcatcaca    420 aaaatcgacg ctcaagtcag aggtggcgaa acccgacagg actataaaga taccaggcgt    480 ttcccctgg aagctccctc gtgcgctctc ctgttccgac cctgccgctt accggatacc    540
tgtccgcctt tctcccttcg ggaagcgtgg cgctttctca tagctcacgc tgtaggtatc    600
tcagttcggt gtaggtcgtt cgctccaagc tgggctgtgt gcacgaaccc cccgttcagc    660
ccgaccgctg cgccttatcc ggtaactatc gtcttgagtc aacccggta agacacgact    720 tatcgccact ggcagcagcc actggtaaca ggattagcag agcgaggtat gtaggcggtg    780
ctacagagtt cttgaagtgg tggcctaact acggctacac tagaaggaca gtatttggta    840
tctgcgctct gctgaagcca gttaccttcg gaaaaagagt tggtagctct tgatccggca    900
aacaaaccac cgctggtagc ggtggttttt ttgtttgcaa gcagcagatt acgcgcagaa    960
aaaaaggatc tcaagaagat cctttgatct tttctacggg gtctgacgct cagtggaacg   1020
aaaactcacg ttaagggatt ttggtcatga gattatcaaa aaggatcttc acctagatcc   1080 tttaaatta aaaatgaagt tttaaatcaa tctaaagtat atatgagtaa acttggtctg    1140
acagttacca atgcttaatc agtgaggcac ctatctcagc gatctgtcta tttcgttcat   1200
ccatagttgc ctgactcccc gtcgtgtaga taactacgat acgggagggc ttaccatctg   1260
gccccagtgc tgcaatgata ccgcgagacc cacgctcacc ggctccagat ttatcagcaa   1320
taaaccagcc agccggaagg gccgagcgca gaagtggtcc tgcaacttta tccgcctcca   1380
```

```
tccagtctat taattgttgc cgggaagcta gagtaagtag ttcgccagtt aatagtttgc    1440
gcaacgttgt tgccattgct acaggcatcg tggtgtcacg ctcgtcgttt ggtatggctt    1500
cattcagctc cggttcccaa cgatcaaggc gagttacatg atcccccatg ttgtgcaaaa    1560
aagcggttag ctccttcggt cctccgatcg ttgtcagaag taagttggcc gcagtgttat    1620
cactcatggt tatggcagca ctgcataatt ctcttactgt catgccatcc gtaagatgct    1680
tttctgtgac tggtgagtac tcaaccaagt cattctgaga atagtgtatg cggcgaccga    1740
gttgctcttg cccggcgtca atacgggata ataccgcgcc acatagcaga actttaaaag    1800
tgctcatcat tggaaaacgt tcttcggggc gaaaactctc aaggatctta ccgctgttga    1860
gatccagttc gatgtaaccc actcgtgcac ccaactgatc ttcagcatct tttactttca    1920
ccagcgtttc tgggtgagca aaaacaggaa ggcaaaatgc cgcaaaaaag gaataagggg    1980
cgacacggaa atgttgaata ctcatactct tcctttttca atattattga agcatttatc    2040
agggttattg tctcatgagc ggatacatat ttgaatgtat ttagaaaaat aaacaaatag    2100
gggttccgcg cacatttccc cgaaaagtgc cacctgacgt ctaagaaacc attattatca    2160
tgacattaac ctataaaaat aggcgtatca cgaggccctt tcgtcttcaa gaattaattc    2220
gggaataaga ttcaacgcca gtcccgaacg tgaaatttcc tctcttgctg gcgcgattgc    2280
agctgtggtg tcatggtcgg tgatcgccag ggtgccgacg cgcatctcga ctgcacggtg    2340
caccaatgct tctggcgtca ggcagccatc ggaagctgtg gtatggctgt gcaggtcgta    2400
aatcactgca taattcgtgt cgctcaaggc gcactcccgt tctggataat gttttttgcg    2460
ccgacatcat aacggttctg gcaaatattc tgaaatgagc tgttgacaat taatcatcga    2520
actagttaac tagtacgcaa gttcacgtaa aagggtatc gattccatgg tagataaaag    2580
aatggcttta gttgaattga agtgcccga cattggcgga cacgaaaatg tagatattat    2640
cgcggttgaa gtaaacgtgg gcgacactat tgctgtggac gataccctga ttactttgga    2700
tctagatatg agcacgaatc ctaaacctca agaaaaaacc aaacgtaaca ccaaccgccg    2760
cccacaggac gtcaagttcc cgggcggtgg tcagatcgtt ggtggagttt acctgttgcc    2820
gcgcaggggc cccaggttgg gtgtgcgcgc aactaggaag cttagtcaga aaatccagct    2880
tgtaaatacc aacggcagct ggcatattaa ccggactgcc ctgaactgca acgactccct    2940
ccagaccggg ttccttgctg cgttgtttta cgtgcacagg ttcaactcgt ccggatgctc    3000
agatcgcatg gccagctgcc gccccattga tacgttcgac caggggtggg gccccattac    3060
ttacgctgag ccgcgcagct tggaccagag gccctattgc tggcactacg cacctcaacc    3120
gtgtggtatc gtaccgcgcg cggaggtgtg tggtccagtg tattgtttca ctccaagccc    3180
cgttgtcgtg gggaccaccg atcgttccgg cgtccctacg tataactggg gggagaatga    3240
gacggacgtg ctgctcctta ctcgagcctc cgcctatgag gtgcgcaacg cgtccgggt    3300 gtaccatgtc acgaacgact gctccaactc aagcattgtg tatgaggcag acgacatgat    3360
catgggatcc                                                          3370
```

<210> SEQ ID NO 2  
<211> LENGTH: 3370  
<212> TYPE: DNA  
<213> ORGANISM: Artificial Sequence  
<220> FEATURE:  
<223> OTHER INFORMATION: Artificial Sequence Description: Sequence corresponding to pIME64K plasmid

<400> SEQUENCE: 2

```
gatcccgggc acaccatcac catcaccatt aagatccggt ggatgacctt tgaatgacc      60
tttaatagat tatattacta attaattggg gaccctagag gtccctttt tatttaaaa      120
attttttcac aaaacggttt acaagcataa agctctgcat taatgaatcg gccaacgcgc    180
ggggagaggc ggtttgcgta ttgggcgctc ttccgcttcc tcgctcactg actcgctgcg    240
ctcggtcgtt cggctgcggc gagcggtatc agctcactca aaggcggtaa tacggttatc    300
cacagaatca ggggataacg caggaaagaa catgtgagca aaaggccagc aaaaggccag    360
gaaccgtaaa aaggccgcgt tgctggcgtt tttccatagg ctccgccccc ctgacgagca    420
tcacaaaaat cgacgctcaa gtcagaggtg gcgaaacccg acaggactat aaagatacca    480
ggcgtttccc cctggaagct ccctcgtgcg ctctcctgtt ccgaccctgc cgcttaccgg    540
atacctgtcc gcctttctcc cttcgggaag cgtggcgctt tctcatagct cacgctgtag    600
gtatctcagt tcggtgtagg tcgttcgctc caagctgggc tgtgtgcacg aacccccgt     660
tcagcccgac cgctgcgcct tatccggtaa ctatcgtctt gagtccaacc cggtaagaca    720
cgacttatcg ccactggcag cagccactgg taacaggatt agcagagcga ggtatgtagg    780
cggtgctaca gagttcttga agtggtggcc taactacggc tacactagaa ggacagtatt    840
tggtatctgc gctctgctga agccagttac cttcggaaaa agagttggta gctcttgatc    900
cggcaaacaa accaccgctg gtagcggtgg ttttttgtt tgcaagcagc agattacgcg     960
cagaaaaaaa ggatctcaag aagatccttt gatcttttct acggggtctg acgctcagtg   1020
gaacgaaaac tcacgttaag ggattttggt catgagatta tcaaaagga tcttaccta     1080
gatcctttta aattaaaaat gaagttttaa atcaatctaa agtatatatg agtaaacttg    1140
gtctgacagt taccaatgct taatcagtga ggcacctatc tcagcgatct gtctatttcg    1200
ttcatccata gttgcctgac tccccgtcgt gtagataact acgatacggg agggcttacc    1260
atctggcccc agtgctgcaa tgataccgcg agacccacgc tcaccggctc cagatttatc    1320
agcaataaac cagccagccg gaagggccga gcgcagaagt ggtcctgcaa ctttatccgc    1380
ctccatccag tctattaatt gttgccggga agctagagta agtagttcgc cagttaatag    1440
tttgcgcaac gttgttgcca ttgctacagg catcgtggtg tcacgctcgt cgtttggtat    1500
ggcttcattc agctccggtt cccaacgatc aaggcgagtt acatgatccc ccatgttgtg    1560
caaaaaagcg gttagctcct tcggtcctcc gatcgttgtc agaagtaagt tggccgcagt    1620
gttatcactc atggttatgg cagcactgca taattctctt actgtcatgc catccgtaag    1680
atgcttttct gtgactggtg agtactcaac caagtcattc tgagaatagt gtatgcggcg    1740
accgagttgc tcttgcccgg cgtcaatacg ggataatacc gcgccacata gcagaacttt    1800
aaaagtgctc atcattggaa aacgttcttc ggggcgaaaa ctctcaagga tcttaccgct    1860
gttgagatcc agttcgatgt aacccactcg tgcacccaac tgatcttcag catctttac    1920
tttcaccagc gtttctgggt gagcaaaaac aggaaggcaa aatgccgcaa aaagggaat    1980
aagggcgaca cggaaatgtt gaatactcat actcttcctt tttcaatatt attgaagcat   2040
ttatcagggt tattgtctca tgagcggata catatttgaa tgtatttaga aaaataaaca    2100
aataggggtt ccgcgcacat ttccccgaaa agtgccacct gacgtctaag aaaccattat    2160
tatcatgaca ttaacctata aaaataggcg tatcacgagg ccctttcgtc ttcaagaatt    2220
aattcgggaa taagattcaa cgccagtccc gaacgtgaaa tttcctctct tgctggcgcg    2280
attgcagctg tggtgtcatg gtcggtgatc gccagggtgc cgacgcgcat ctcgactgca    2340
cggtgcacca atgcttctgg cgtcaggcag ccatcggaag ctgtggtatg gctgtgcagg    2400
```

```
tcgtaaatca ctgcataatt cgtgtcgctc aaggcgcact cccgttctgg ataatgtttt    2460
ttgcgccgac atcataacgg ttctggcaaa tattctgaaa tgagctgttg acaattaatc    2520
atcgaactag ttaactagta cgcaagttca cgtaaaaagg gtatcgattc catggtagat    2580
aaaagaatgg ctttagttga attgaaagtg cccgacattg gcggacacga aaatgtagat    2640
attatcgcgg ttgaagtaaa cgtgggcgac actattgctg tggacgatac cctgattact    2700
ttggatctag atagtcagaa aatccagctt gtaaatacca acggcagctg gcatattaac    2760
cggactgccc tgaactgcaa cgactccctc cagaccgggt tccttgctgc gttgttttac    2820
gtgcacaggt tcaactcgtc cggatgctca gatcgcatgg ccagctgccg ccccattgat    2880
acgttcgacc aggggtgggg ccccattact tacgctgagc cgcgcagctt ggaccagagg    2940
ccctattgct ggcactacgc acctcaaccg tgtggtatcg tacccgcggc ggaggtgtgt    3000
ggtccagtgt attgtttcac tccaagcccc gttgtcgtgg ggaccaccga tcgttccggc    3060
gtccctacgt ataactgggg ggagaatgag acggacgtgc tgctccttaa gcttcctcc     3120 gcctatgagg tgcgcaacgc gtccggggtg taccatgtca cgaacgactg ctccaactca    3180
agcattgtgt atgaggcaga cgacatgatc atgctcgaga tgagcacgaa tcctaaacct    3240
caaagaaaaa ccaaacgtaa caccaaccgc cgcccacagg acgtcaagtt cccgggcggt    3300
ggtcagatcg ttggtggagt ttacctgttg ccgcgcaggg gccccaggtt gggtgtgcgc    3360
gcaactaggg                                                          3370

<210> SEQ ID NO 3
<211> LENGTH: 3370
<212> TYPE: DNA
<213> ORGANISM: Artificial Sequence
<220> FEATURE:
<223> OTHER INFORMATION: Artificial Sequence Description: Sequence
      corresponding to pIME164K plasmid

<400> SEQUENCE: 3
ttcgggaata agattcaacg ccagtcccga acgtgaaatt tcctctcttg ctggcgcgat      60
tgcagctgtg gtgtcatggt cggtgatcgc cagggtgccg acgcgcatct cgactgcacg    120
gtgcaccaat gcttctggcg tcaggcagcc atcggaagct gtggtatggc tgtgcaggtc    180
gtaaatcact gcataattcg tgtcgctcaa ggcgcactcc cgttctggat aatgtttttt    240
gcgccgacat cataacggtt ctggcaaata ttctgaaatg agctgttgac aattaatcat    300
cgaactagtt aactagtacg caagttcacg taaaaagggt atcgattcca tggtagataa    360
aagaatggct ttagttgaat gaaagtgccc gacattggc ggacacgaaa atgtagatat     420
tatcgcggtt gaagtaaacg tgggcgacac tattgctgtg gacgataccc tgattacttt    480
ggatctagat ccgcctatg aggtgcgcaa cgcgtccggg gtgtaccatg tcacgaacga    540
ctgctccaac tcaagcattg tgtatgaggc agacgacatg atcatgaaag cttccagtca    600
gaaaatccag cttgtaaata ccaacggcag ctggcatatt aaccgactgc cctgaactg     660 caacgactcc ctccagaccg ggttccttgc tgcgttgttt tacgtgcaca ggttcaactc    720
gtccggatgc tcagatcgca tggccagctg ccgccccatt gatacgttcg accagggggtg    780 gggcccccatt acttacgctg agccgcgcag cttggaccag aggcccctatt gctggcacta    840 cgcacctcaa ccgtgtggta tcgtacccgc ggcggaggtg tgtggtccag tgtattgttt    900
cactccaagc cccgttgtcg tggggaccac cgatcgttcc ggcgtcccta cgtataactg    960
gggggagaat gagacggacg tgctgctcct tctcgagatg agcacgaatc ctaaacctca    1020
```

```
aagaaaaacc aaacgtaaca ccaaccgccg cccacaggac gtcaagttcc cgggcggtgg    1080
tcagatcgtt ggtggagttt acctgttgcc gcgcaggggc cccaggttgg gtgtgcgcgc    1140
aactagggga tcccgggcac accatcacca tcaccattaa gatccggtgg atgaccttt     1200 gaatgacctt taatagatta tattactaat taattgggga ccctagaggt cccttttta    1260 ttttaaaaat tttttcacaa aacggtttac aagcataaag ctctgcatta atgaatcggc    1320
caacgcgcgg ggagaggcgg tttgcgtatt gggcgctctt ccgcttcctc gctcactgac    1380
tcgctgcgct cggtcgttcg gctgcggcga gcggtatcag ctcactcaaa ggcggtaata    1440
cggttatcca cagaatcagg ggataacgca ggaaagaaca tgtgagcaaa aggccagcaa    1500
aaggccagga accgtaaaaa ggccgcgttg ctggcgtttt tccataggct ccgcccccct    1560
gacgagcatc acaaaaatcg acgctcaagt cagaggtggc gaaacccgac aggactataa    1620
agataccagg cgtttccccc tggaagctcc ctcgtgcgct ctcctgttcc gaccctgccg    1680
cttaccggat acctgtccgc ctttctccct tcgggaagcg tggcgctttc tcatagctca    1740
cgctgtaggt atctcagttc ggtgtaggtc gttcgctcca agctgggctg tgtgcacgaa    1800
ccccccgttc agcccgaccg ctgcgcctta tccggtaact atcgtcttga gtccaacccg    1860
gtaagacacg acttatcgcc actggcagca gccactggta acaggattag cagagcgagg    1920
tatgtaggcg gtgctacaga gttcttgaag tggtggccta actacggcta cactagaagg    1980
acagtatttg gtatctgcgc tctgctgaag ccagttacct tcggaaaaag agttggtagc    2040
tcttgatccg gcaaacaaac caccgctggt agcggtggtt ttttttgtttg caagcagcag    2100 attacgcgca gaaaaaaagg atcctttga tcttttctac ggggtctgac    2160
gctcagtgga acgaaaactc acgttaaggg attttggtca tgagattatc aaaaaggatc    2220
ttcacctaga tccttttaaa ttaaaaatga agttttaaat caatctaaag tatatatgag    2280
taaacttggt ctgacagtta ccaatgctta atcagtgagg cacctatctc agcgatctgt    2340
ctatttcgtt catccatagt tgcctgactc cccgtcgtgt agataactac gatacgggag    2400
ggcttaccat ctggccccag tgctgcaatg ataccgcgag acccacgctc accggctcca    2460
gatttatcag caataaacca gccagccgga agggccgagc gcagaagtgg tcctgcaact    2520
ttatccgcct ccatccagtc tattaattgt tgccgggaag ctagagtaag tagttcgcca    2580
gttaatagtt tgcgcaacgt tgttgccatt gctacaggca tcgtggtgtc acgctcgtcg    2640
tttggtatgg cttcattcag ctccggttcc caacgatcaa ggcgagttac atgatccccc    2700
atgttgtgca aaaaagcggt tagctccttc ggtcctccga tcgttgtcag aagtaagttg    2760
gccgcagtgt tatcactcat ggttatggca gcactgcata attctcttac tgtcatgcca    2820
tccgtaagat gcttttctgt gactggtgag tactcaacca agtcattctg agaatagtgt    2880
atgcggcgac cgagttgctc ttgcccggcg tcaatacggg ataataccgc gccacatagc    2940
agaactttaa aagtgctcat cattggaaaa cgttcttcgg ggcgaaaact ctcaaggatc    3000
ttaccgctgt tgagatccag ttcgatgtaa cccactcgtg cacccaactg atcttcagca    3060
tcttttactt tcaccagcgt ttctgggtga gcaaaaacag gaaggcaaaa tgccgcaaaa    3120
aagggaataa gggcgacacg gaaatgttga atactcatac tcttcctttt tcaatattat    3180
tgaagcattt atcagggtta ttgtctcatg agcggataca tatttgaatg tatttagaaa    3240
aataaacaaa taggggttcc gcgcacattt ccccgaaaag tgccacctga cgtctaagaa    3300
accattatta tcatgacatt aacctataaa aataggcgta tcacgaggcc ctttcgtctt    3360
```
caagaattaa 3370

<210> SEQ ID NO 4
<211> LENGTH: 3541
<212> TYPE: DNA
<213> ORGANISM: Artificial Sequence
<220> FEATURE:
<223> OTHER INFORMATION: Artificial Sequence Description: Sequence corresponding to pINSE64K plasmid

<400> SEQUENCE: 4

```
tgctcgagta cctggtggcc taccaggcca ccgtgtgcgc ccgcgcccag gccccccccc      60
ccagctgggc cgcctacggc tacaaggtga tcgtgctgaa ccccgcgtg gccagcaccc     120
tggccgccta cctgcccgag tacgtgatca tggtgaagct gcccagccgc gccctcgaga     180
tgagcacgaa tcctaaacct caagaaaaaa ccaaacgtaa caccaaccgc cgcccacagg     240
acgtcaagtt cccgggcggt ggtcagatcg ttggtggagt ttacctgttg ccgcgcaggg     300
gccccaggtt gggtgtgcgc gcaactaggg gatcccgggc acaccatcac catcaccatt     360
aagatccggt ggatgacctt tgaatgaccc tttaatagat tatattacta attaattggg     420
gacccctagag gtccctttttt tattttaaaa attttttcac aaaacggttt acaagcataa     480
agctctgcat taatgaatcg gccaacgcgc ggggagaggc ggtttgcgta ttgggcgctc     540
ttccgcttcc tcgctcactg actcgctgcg ctcggtcgtt cggctgcggc gagcggtatc     600
agctcactca aaggcggtaa tacggttatc cacagaatca ggggataacg caggaaagaa     660
catgtgagca aaaggccagc aaaaggccag gaaccgtaaa aaggccgcgt tgctggcgtt     720
tttccatagg ctccgccccc ctgacgagca tcacaaaaat cgacgctcaa gtcagaggtg     780
gcgaaacccg acaggactat aaagatacca ggcgtttccc cctggaagct ccctcgtgcg     840
ctctcctgtt ccgaccctgc cgcttaccgg atacctgtcc gcctttctcc cttcgggaag     900
cgtggcgctt tctcatagct cacgctgtag gtatctcagt tcggtgtagg tcgttcgctc     960
caagctgggc tgtgtgcacg aaccccccgt tcagcccgac cgctgcgcct tatccggtaa    1020
ctatcgtctt gagtccaacc cggtaagaca cgacttatcg ccactggcag cagccactgg    1080
taacaggatt agcagagcga ggtatgtagg cggtgctaca gagttcttga agtggtggcc    1140
taactacggc tacactagaa ggacagtatt tggtatctgc gctctgctga agccagttac    1200
cttcggaaaa agagttggta gctcttgatc cggcaaacaa accaccgctg gtagcggtgg    1260
tttttttgtt tgcaagcagc agattacgcg cagaaaaaaa ggatctcaag aagatccttt    1320
gatcttttct acggggtctg acgctcagtg gaacgaaaac tcacgttaag ggattttggt    1380
catgagatta tcaaaaagga tcttcaccta gatcctttta aattaaaaat gaagttttaa    1440
atcaatctaa agtatatatg agtaaacttg gtctgacagt taccaatgct taatcagtga    1500
ggcacctatc tcagcgatct gtctatttcg ttcatccata gttgcctgac tccccgtcgt    1560
gtagataact acgatacggg agggcttacc atctggcccc agtgctgcaa tgataccgcg    1620
agacccacgc tcaccggctc cagatttatc agcaataaac cagccagccg aagggccga    1680
gcgcagaagt ggtcctgcaa ctttatccgc ctccatccag tctattaatt gttgccggga    1740
agctagagta agtagttcgc cagttaatag tttgcgcaac gttgttgcca ttgctacagg    1800
catcgtggtg tcacgctcgt cgtttggtat ggcttcattc agctccggtt cccaacgatc    1860
aaggcgagtt acatgatccc ccatgttgtg caaaaaagcg gttagctcct tcggtcctcc    1920
gatcgttgtc agaagtaagt tggccgcagt gttatcactc atggttatgg cagcactgca    1980
```

```
taattctctt actgtcatgc catccgtaag atgcttttct gtgactggtg agtactcaac    2040
caagtcattc tgagaatagt gtatgcggcg accgagttgc tcttgcccgg cgtcaatacg    2100
ggataatacc gcgccacata gcagaacttt aaaagtgctc atcattggaa aacgttcttc    2160
ggggcgaaaa ctctcaagga tcttaccgct gttgagatcc agttcgatgt aacccactcg    2220
tgcacccaac tgatcttcag catcttttac tttcaccagc gtttctgggt gagcaaaaac    2280
aggaaggcaa aatgccgcaa aaaagggaat aagggcgaca cggaaatgtt gaatactcat    2340
actcttcctt tttcaatatt attgaagcat ttatcagggt tattgtctca tgagcggata    2400
catatttgaa tgtatttaga aaataaaca aatagggg ttccgcgcacat tccccgaaa     2460
agtgccacct gacgtctaag aaaccattat tatcatgaca ttaacctata aaaataggcg    2520
tatcacgagg cccttcgtc ttcaagaatt aattcgggaa taagattcaa cgccagtccc    2580
gaacgtgaaa tttcctctct tgctggcgcg attgcagctg tggtgtcatg gtcggtgatc    2640
gccagggtgc cgacgcgcat ctcgactgca cggtgcacca atgcttctgg cgtcaggcag    2700
ccatcggaag ctgtggtatg gctgtgcagg tcgtaaatca ctgcataatt cgtgtcgctc    2760
aaggcgcact cccgttctgg ataatgtttt ttgcgccgac atcataacgg ttctggcaaa    2820
tattctgaaa tgagctgttg acaattaatc atcgaactag ttaactagta cgcaagttca    2880
cgtaaaaagg gtatcgattc catggtagat aaaagaatgg ctttagttga attgaaagtg    2940
cccgacattg gcggacacga aaatgtagat attatcgcgg ttgaagtaaa cgtgggcgac    3000
actattgctg tggacgatac cctgattact ttggatctag atagtcagaa aatccagctt    3060
gtaaatacca acggcagctg gcatattaac cggactgccc tgaactgcaa cgactccctc    3120
cagaccgggt tccttgctgc gttgttttac gtgcacaggt tcaactcgtc cggatgctca    3180
gatcgcatgg ccagctgccg ccccattgat acgttcgacc aggggtgggg ccccattact    3240
tacgctgagc cgcgcagctt ggaccagagg ccctattgct ggcactacgc acctcaaccg    3300
tgtggtatcg tacccgcggc ggaggtgtgt ggtccagtgt attgtttcac tccaagcccc    3360
gttgtcgtgg ggaccaccga tcgttccggc gtccctacgt ataactgggg ggagaatgag    3420
acggacgtgc tgctccttaa agcttcctcc gcctatgagg tgcgcaacgc gtccggggtg    3480
taccatgtca cgaacgactg ctccaactca agcattgtgt atgaggcaga cgacatgatc    3540
a                                                                   3541
```

<210> SEQ ID NO 5
<211> LENGTH: 3565
<212> TYPE: DNA
<213> ORGANISM: Artificial Sequence
<220> FEATURE:
<223> OTHER INFORMATION: Artificial Sequence Description: Sequence
      corresponding to pIENSb plasmid

<400> SEQUENCE: 5

```
tcgagatgag cacgaatcct aaacctcaaa gaaaaaccaa acgtaacacc aaccgccgcc      60
cacaggacgt caagttcccg ggcggtggtc agatcgttgg tggagtttac ctgttgccgc     120
gcaggggccc caggttgggt gtgcgcgcaa ctagggggatc ccgggcacac catcaccatc    180
accattaaga tccggtggat gaccttttga atgacctta atagattata ttactaatta    240
attggggacc ctagaggtcc cttttttatt ttaaaatttt tttcacaaaa cggtttacaa    300
gcataaagct ctgcattaat gaatcggcca acgcgcgggg agaggcggtt tgcgtattgg    360
gcgctcttcc gcttcctcgc tcactgactc gctgcgctcg gtcgttcggc tgcggcgagc    420
```

```
ggtatcagct cactcaaagg cggtaatacg gttatccaca gaatcagggg ataacgcagg    480
aaagaacatg tgagcaaaag gccagcaaaa ggccaggaac cgtaaaaagg ccgcgttgct    540 ggcgttttc catagctcc gccccctga cgagcatcac aaaaatcgac gctcaagtca       600
gaggtggcga acccgacag gactataaag ataccaggcg tttccccctg gaagctccct    660
cgtgcgctct cctgttccga ccctgccgct taccggatac ctgtccgcct ttctcccttc    720
gggaagcgtg cgctttctc atagctcacg ctgtaggtat ctcagttcgg tgtaggtcgt    780
tcgctccaag ctgggctgtg tgcacgaacc ccccgttcag cccgaccgct gcgccttatc    840
cggtaactat cgtcttgagt ccaacccggt aagacacgac ttatcgccac tggcagcagc    900
cactggtaac aggattagca gagcgaggta tgtaggcggt gctacagagt tcttgaagtg    960
gtggcctaac tacggctaca ctagaaggac agtatttggt atctgcgctc tgctgaagcc   1020
agttaccttc ggaaaaagag ttggtagctc ttgatccggc aaacaaacca ccgctggtag   1080
cggtggtttt tttgtttgca agcagcagat tacgcgcaga aaaaaaggat ctcaagaaga   1140
tcctttgatc ttttctacgg ggtctgacgc tcagtggaac gaaaactcac gttaagggat   1200
tttggtcatg agattatcaa aaaggatctt cacctagatc cttttaaatt aaaaatgaag   1260
ttttaaatca atctaaagta tatatgagta aacttggtct gacagttacc aatgcttaat   1320
cagtgaggca cctatctcag cgatctgtct atttcgttca tccatagttg cctgactccc   1380
cgtcgtgtag ataactacga tacggggaggg cttaccatct ggccccagtg ctgcaatgat   1440
accgcgagac ccacgctcac cggctccaga tttatcagca ataaaccagc cagccggaag   1500
ggccgagcgc agaagtggtc ctgcaacttt atccgcctcc atccagtcta ttaattgttg   1560
ccgggaagct agagtaagta gttcgccagt taatagtttg cgcaacgttg ttgccattgc   1620
tacaggcatc gtggtgtcac gctcgtcgtt tggtatggct tcattcagct ccggttccca   1680
acgatcaagg cgagttacat gatccccat gttgtgcaaa aaagcggtta gctccttcgg   1740
tcctccgatc gttgtcagaa gtaagttggc cgcagtgtta tcactcatgg ttatggcagc   1800
actgcataat tctcttactg tcatgccatc cgtaagatgc ttttctgtga ctggtgagta   1860
ctcaaccaag tcattctgag aatagtgtat gcggcgaccg agttgctctt gcccggcgtc   1920
aatacgggat aataccgcgc cacatagcag aactttaaaa gtgctcatca ttggaaaacg   1980
ttcttcgggg cgaaaactct caaggatctt accgctgttg agatccagtt cgatgtaacc   2040
cactcgtgca cccaactgat cttcagcatc ttttactttc accagcgttt ctgggtgagc   2100
aaaaacagga aggcaaaatg ccgcaaaaaa gggaataagg gcgacacgga atgttgaat   2160 actcatactc ttcctttttc aatattattg aagcatttat cagggttatt gtctcatgag   2220
cggatacata tttgaatgta tttagaaaaa taaacaaata ggggttccgc gcacatttcc   2280
ccgaaaagtg ccacctgacg tctaagaaac cattattatc atgacattaa cctataaaaa   2340
taggcgtatc acgaggccct ttcgtcttca agaattaatt cgggaataag attcaacgcc   2400
agtcccgaac gtgaaatttc ctctcttgct ggcgcgattg cagctgtggt gtcatggtcg   2460
gtgatcgcca gggtgccgac gcgcatctcg actgcacggt gcaccaatgc ttctggcgtc   2520
aggcagccat cggaagctgt ggtatggctg tgcaggtcgt aaatcactgc ataattcgtg   2580
tcgctcaagg cgcactcccg ttctggataa tgttttttgc gccgacatca taacggttct   2640
ggcaaatatt ctgaaatgag ctgttgacaa ttaatcatcg aactagttaa ctagtacgca   2700
agttcacgta aaagggtat cgattccatg gtagataaaa gaatggcttt agttgaattg   2760
aaagtgcccg acattggcgg acacgaaaat gtagatatta tcgcggttga agtaaacgtg   2820
```

```
ggcgacacta ttgctgtgga cgatacccctg attactttgg atctagatag tcagaaaatc    2880
cagcttgtaa ataccaacgg cagctggcat attaaccgga ctgcccctgaa ctgcaacgac    2940 tccctccaga ccgggttcct tgctgcgttg ttttacgtgc acaggttcaa ctcgtccgga    3000
tgctcagatc gcatggccag ctgccgcccc attgatacgt tcgaccaggg gtggggcccc    3060
attacttacg ctgagccgcg cagcttggac cagaggccct attgctggca ctacgcacct    3120
caaccgtgtg gtatcgtacc cgcggcggag gtgtgtggtc cagtgtattg tttcactcca    3180
agccccgttg tcgtggggac caccgatcgt tccggcgtcc ctacgtataa ctgggggag    3240 aatgagacgg acgtgctgct ccttaaagct tcctccgcct atgaggtgcg caacgcgtcc    3300
ggggtgtacc atgtcacgaa cgactgctcc aactcaagca ttgtgtatga ggcagacgac    3360
atgatcatgc tcgagagatc tggccgccac ctgatcttct gccacagcaa gaagaagtgc    3420
gacgagctgg ccaccaagct ggccgcctac tacctggtgg cctaccaggc caccgtgtgc    3480
gcccgcgccc aggccccccc ccccagctgg gccgcctacg gctacaaggt gatcgtgctg    3540
aacccccgcg tggccagcac cctgc                                          3565
```

<210> SEQ ID NO 6
<211> LENGTH: 3904
<212> TYPE: DNA
<213> ORGANISM: Artificial Sequence
<220> FEATURE:
<223> OTHER INFORMATION: Artificial Sequence Description: Sequence
      corresponding to pIENS3 plasmid

<400> SEQUENCE: 6

```
cgcactcccg ttctggataa tgttttttgc gccgacatca taacggttct ggcaaatatt      60
ctgaaatgag ctgttgacaa ttaatcatcg aactagttaa ctagtacgca agttcacgta     120
aaaagggtat cgattccatg gtagataaaa gaatggcttt agttgaattg aaagtgcccg     180
acattggcgg acacgaaaat gtagatatta tcgcggttga agtaaacgtg ggcgacacta     240
ttgctgtgga cgatacccctg attactttgg atctagatag tcagaaaatc cagcttgtaa     300
ataccaacgg cagctggcat attaaccgga ctgcccctgaa ctgcaacgac tccctccaga     360
ccgggttcct tgctgcgttg ttttacgtgc acaggttcaa ctcgtccgga tgctcagatc     420
gcatggccag ctgccgcccc attgatacgt tcgaccaggg gtggggcccc attacttacg     480
ctgagccgcg cagcttggac cagaggccct attgctggca ctacgcacct caaccgtgtg     540
gtatcgtacc cgcggcggag gtgtgtggtc cagtgtattg tttcactcca agccccgttg     600
tcgtggggac caccgatcgt tccggcgtcc ctacgtataa ctgggggag aatgagacgg      660 acgtgctgct ccttaaagct tcctccgcct atgaggtgcg caacgcgtcc ggggtgtacc     720
atgtcacgaa cgactgctcc aactcaagca ttgtgtatga ggcagacgac atgatcatgc     780
tcgagagatc tgcggcgtat gcggcgcagg gctataaagt gctggtgctg aacccgagcg     840
tggcggcgac cctgggcttt ggcgcgtata tgagcaaagc gcatggcatt gatccgaaca     900
ttcgtaccgg cgtgcgtacc attaccaccg gcagcccgat tacctatagc acctatggca     960
aatttctggc ggatgcggc tgcagcgcg gcgcgtatga tattattatt tgcgatgaat     1020
gccatagcac cgatgcgacc agcattctgg gcattggcac cgtgctggat caggcggaaa     1080
ccgcgggcgc gcgtctggtg gtgctggcga ccgcgacccc gccgggcagc gtgaccgtgc     1140
cgcatccgaa cattgaagaa gtggcgctga gcaccaccgg cgaaattccg ttttatggca     1200
aagcgattcc gctggaagtt attaaaggcg gccgtcatct gatttttttgc cacagcaaaa     1260
```

```
aaaaatgcga tgaactggcg gcgaaactgg tggcgctggg cattaacgcg gtgctcgaga    1320
tgagcacgaa tcctaaacct caaagaaaaa ccaaacgtaa caccaaccgc cgcccacagg    1380
acgtcaagtt cccgggcggt ggtcagatcg ttggtggagt ttacctgttg ccgcgcaggg    1440
gccccaggtt gggtgtgcgc gcaactaggg gatcccgggc acaccatcac catcaccatt    1500
aagatccggt ggatgacctt ttgaatgacc tttaatagat tatattacta attaattggg    1560 gacccctagag gtccctttttt tatttttaaaa attttttcac aaaacggttt acaagcataa    1620
agctctgcat taatgaatcg gccaacgcgc ggggagaggc ggtttgcgta ttgggcgctc    1680
ttccgcttcc tcgctcactg actcgctgcg ctcggtcgtt cggctgcggc gagcggtatc    1740
agctcactca aaggcggtaa tacggttatc cacagaatca ggggataacg caggaaagaa    1800
catgtgagca aaaggccagc aaaaggccag gaaccgtaaa aaggccgcgt tgctggcgtt    1860
tttccatagg ctccgccccc ctgacgagca tcacaaaaat cgacgctcaa gtcagaggtg    1920
gcgaaacccg acaggactat aaagatacca ggcgtttccc cctggaagct ccctcgtgcg    1980
ctctcctgtt ccgaccctgc cgcttaccgg atacctgtcc gcctttctcc cttcgggaag    2040
cgtggcgctt tctcatagct cacgctgtag gtatctcagt tcggtgtagg tcgttcgctc    2100
caagctgggc tgtgtgcacg aaccccccgt tcagcccgac cgctgcgcct tatccggtaa    2160
ctatcgtctt gagtccaacc cggtaagaca cgacttatcg ccactggcag cagccactgg    2220
taacaggatt agcagagcga ggtatgtagg cggtgctaca gagttcttga agtggtggcc    2280
taactacggc tacactagaa ggacagtatt tggtatctgc gctctgctga gccagttac    2340 cttcggaaaa agagttggta gctcttgatc cggcaaacaa accaccgctg gtagcggtgg    2400 ttttttttgtt tgcaagcagc agattacgcg cagaaaaaaa ggatctcaag aagatccttt    2460
gatcttttct acggggtctg acgctcagtg gaacgaaaac tcacgttaag ggattttggt    2520
catgagatta tcaaaaagga tcttcaccta gatcctttta aattaaaaat gaagttttaa    2580
atcaatctaa agtatatatg agtaaacttg gtctgacagt taccaatgct taatcagtga    2640
ggcacctatc tcagcgatct gtctatttcg ttcatccata gttgcctgac tccccgtcgt    2700
gtagataact acgatacggg agggcttacc atctggcccc agtgctgcaa tgataccgcg    2760
agacccacgc tcaccggctc cagatttatc agcaataaac cagccagccg gaagggccga    2820
gcgcagaagt ggtcctgcaa ctttatccgc ctccatccag tctattaatt gttgccggga    2880
agctagagta agtagttcgc cagttaatag tttgcgcaac gttgttgcca ttgctacagg    2940
catcgtggtg tcacgctcgt cgtttggtat ggcttcattc agctccggtt cccaacgatc    3000
aaggcgagtt acatgatccc ccatgttgtg caaaaaagcg gttagctcct tcggtcctcc    3060
gatcgttgtc agaagtaagt tggccgcagt gttatcactc atggttatgg cagcactgca    3120
taattctctt actgtcatgc catccgtaag atgcttttct gtgactggtg agtactcaac    3180
caagtcattc tgagaatagt gtatgcggcg accgagttgc tcttgcccgg cgtcaatacg    3240
ggataatacc gcgccacata gcagaacttt aaaagtgctc atcattggaa aacgttcttc    3300
ggggcgaaaa ctctcaagga tcttaccgct gttgagatcc agttcgatgt aacccactcg    3360
tgcacccaac tgatcttcag catcttttac tttcaccagc gtttctgggt gagcaaaaac    3420
aggaaggcaa aatgccgcaa aaaagggaat aagggcgaca cggaaatgtt gaatactcat    3480
actcttcctt tttcaatatt attgaagcat ttatcagggt tattgtctca tgagcggata    3540
catatttgaa tgtatttaga aaaataaaca aataggggtt ccgcgcacat ttccccgaaa    3600
```

-continued

| | |
|---|---|
| agtgccacct gacgtctaag aaaccattat tatcatgaca ttaacctata aaaataggcg | 3660 |
| tatcacgagg ccctttcgtc ttcaagaatt aattcgggaa taagattcaa cgccagtccc | 3720 |
| gaacgtgaaa tttcctctct tgctggcgcg attgcagctg tggtgtcatg gtcggtgatc | 3780 |
| gccagggtgc cgacgcgcat ctcgactgca cggtgcacca atgcttctgg cgtcaggcag | 3840 |
| ccatcggaag ctgtggtatg gctgtgcagg tcgtaaatca ctgcataatt cgtgtcgctc | 3900 |
| aagg | 3904 |

<210> SEQ ID NO 7
<211> LENGTH: 3418
<212> TYPE: DNA
<213> ORGANISM: Artificial Sequence
<220> FEATURE:
<223> OTHER INFORMATION: Artificial Sequence Description: Sequence
      corresponding to pIMP1E64K plasmid

<400> SEQUENCE: 7

| | |
|---|---|
| tcgagctgcc cgagtacgtg atcatggtga agctgcccag ccgcgccctc gagatgagca | 60 |
| cgaatcctaa acctcaaaga aaaccaaac gtaacaccaa ccgccgccca caggacgtca | 120 |
| agttcccggg cggtggtcag atcgttggtg gagtttacct gttgccgcgc aggggcccca | 180 |
| ggttgggtgt gcgcgcaact aggggatccc gggcacacca tcaccatcac cattaagatc | 240 |
| cggtggatga cctttttgaat gacctttaat agattatatt actaattaat tggggaccct | 300 |
| agaggtccct tttttatttt aaaaattttt tcacaaaacg gtttacaagc ataaagctct | 360 |
| gcattaatga atcggccaac gcgcggggag aggcggtttg cgtattgggc gctcttccgc | 420 |
| ttcctcgctc actgactcgc tgcgctcggt cgttcggctg cggcgagcgg tatcagctca | 480 |
| ctcaaaggcg gtaatacggt tatccacaga atcaggggat aacgcaggaa agaacatgtg | 540 |
| agcaaaaggc cagcaaaagg ccaggaaccg taaaaaggcc gcgttgctgg cgttttttcca | 600 |
| taggctccgc cccctgacg agcatcacaa aaatcgacgc tcaagtcaga ggtggcgaaa | 660 |
| cccgacagga ctataaagat accaggcgtt tcccctgga agctccctcg tgcgctctcc | 720 |
| tgttccgacc ctgccgctta ccggatacct gtccgccttt ctcccttcgg gaagcgtggc | 780 |
| gctttctcat agctcacgct gtaggtatct cagttcggtg taggtcgttc gctccaagct | 840 |
| gggctgtgtg cacgaacccc ccgttcagcc cgaccgctgc gccttatccg gtaactatcg | 900 |
| tcttgagtcc aacccggtaa gacacgactt atcgccactg gcagcagcca ctggtaacag | 960 |
| gattagcaga gcgaggtatg taggcggtgc tacagagttc ttgaagtggt ggcctaacta | 1020 |
| cggctacact agaaggacag tatttggtat ctgcgctctg ctgaagccag ttaccttcgg | 1080 |
| aaaaagagtt ggtagctctt gatccggcaa acaaaccacc gctggtagcg tggtttttt | 1140 |
| tgtttgcaag cagcagatta cgcgcagaaa aaaggatct caagaagatc ctttgatctt | 1200 |
| ttctacgggg tctgacgctc agtggaacga aaactcacgt taagggattt tggtcatgag | 1260 |
| attatcaaaa aggatcttca cctagatcct ttaaattaa aatgaagtt ttaaatcaat | 1320 |
| ctaaagtata tatgagtaaa cttggtctga cagttaccaa tgcttaatca gtgaggcacc | 1380 |
| tatctcagcg atctgtctat ttcgttcatc catagttgcc tgactccccg tcgtgtagat | 1440 |
| aactacgata cgggagggct taccatctgg ccccagtgct gcaatgatac cgcgagaccc | 1500 |
| acgctcaccg gctccagatt tatcagcaat aaaccagcca gccggaaggg ccgagcgcag | 1560 |
| aagtggtcct gcaactttat ccgcctccat ccagtctatt aattgttgcc gggaagctag | 1620 |
| agtaagtagt tcgccagtta atagtttgcg caacgttgtt gccattgcta caggcatcgt | 1680 |

```
ggtgtcacgc tcgtcgtttg gtatggcttc attcagctcc ggttcccaac gatcaaggcg    1740
agttacatga tcccccatgt tgtgcaaaaa agcggttagc tccttcggtc ctccgatcgt    1800
tgtcagaagt aagttggccg cagtgttatc actcatggtt atggcagcac tgcataattc    1860
tcttactgtc atgccatccg taagatgctt ttctgtgact ggtgagtact caaccaagtc    1920
attctgagaa tagtgtatgc ggcgaccgag ttgctcttgc ccggcgtcaa tacgggataa    1980
taccgcgcca catagcagaa ctttaaaagt gctcatcatt ggaaaacgtt cttcggggcg    2040
aaaactctca aggatcttac cgctgttgag atccagttcg atgtaaccca ctcgtgcacc    2100
caactgatct tcagcatctt ttactttcac cagcgtttct gggtgagcaa aacaggaag    2160 gcaaaatgcc gcaaaaaagg gaataagggc gacacggaaa tgttgaatac tcatactctt    2220
cctttttcaa tattattgaa gcatttatca gggttattgt ctcatgagcg gatacatatt    2280
tgaatgtatt tagaaaaata acaaataggg gttccgcgc acatttcccc gaaaagtgcc    2340
acctgacgtc taagaaacca ttattatcat gacattaacc tataaaaata ggcgtatcac    2400
gaggcccttt cgtcttcaag aattaattcg ggaataagat tcaacgccag tcccgaacgt    2460
gaaatttcct ctcttgctgg cgcgattgca gctgtggtgt catggtcggt gatcgccagg    2520
gtgccgacgc gcatctcgac tgcacggtgc accaatgctt ctggcgtcag gcagccatcg    2580
gaagctgtgg tatggctgtg caggtcgtaa atcactgcat aattcgtgtc gctcaaggcg    2640
cactcccgtt ctggataatg ttttttgcgc cgacatcata acggttctgg caaatattct    2700
gaaatgagct gttgacaatt aatcatcgaa ctagttaact agtacgcaag ttcacgtaaa    2760
aagggtatcg attccatggt agataaaaga atggctttag ttgaattgaa agtgcccgac    2820
attggcggac acgaaaatgt agatattatc gcggttgaag taaacgtggg cgacactatt    2880
gctgtgacga tacccctgat tactttggat ctagatagtc agaaaatcca gcttgtaaat    2940
accaacggca gctggcatat taaccggact gccctgaact gcaacgactc cctccagacc    3000
gggttccttg ctgcgttgtt ttacgtgcac aggttcaact cgtccggatg ctcagatcgc    3060
atggccagct gccgccccat tgatacgttc gaccaggggt ggggcccccat tacttacgct    3120 gagccgcgca gcttggacca gaggcccctat tgctggcact acgcacctca accgtgtggt    3180
atcgtacccg cggcggaggt gtgtggtcca gtgtattgtt tcactccaag ccccgttgtc    3240
gtggggacca ccgatcgttc cggcgtccct acgtataact gggggagaa tgagacggac    3300 gtgctgctcc ttaaagcttc ctccgcctat gaggtgcgca acgcgtccgg ggtgtaccat    3360
gtcacgaacg actgctccaa ctcaagcatt gtgtatgagg cagacgacat gatcatgc     3418
```

<210> SEQ ID NO 8
<211> LENGTH: 3370
<212> TYPE: DNA
<213> ORGANISM: Artificial Sequence
<220> FEATURE:
<223> OTHER INFORMATION: Artificial Sequence Description: Sequence corresponding to pIME64Kb plasmid

<400> SEQUENCE: 8

```
atggtagata aaagaatggc tttagttgaa ttgaaagtgc ccgacattgg cggacacgaa      60
aatgtagata ttatcgcggt tgaagtaaac gtgggcgaca ctattgctgt ggacgatacc     120
ctgattactt tggatctaga taagcagaac atccaactga tcaacaccaa cggcagttgg     180
cacatcaata gcacggcctt gaactgcaat gaaagcctta acaccggctg gttagcaggg     240
ctcttctatc agcacaaatt caactcttca ggctgtcctg agaggttggc cagctgccga     300
```

```
cgccttaccg attttgccca gggctggggt cctatcagtt atgccaacgg aagcggcctc    360
gacgaacgcc cctactgctg cactaccct ccaagacctt gtggcattgt gcccgcaaag    420
agcgtgtgtg gcccggtata ttgcttcact cccagccccg tggtggtggg aacgaccgac    480
aggtcgggcg cgcctaccta cagctggggt gcaaatgata cggatgtctt cgtccttaaa    540
gcttcctcag cctaccaagt gcgcaattcc tcggggcttt accatgtcac caatgattgc    600
cctaactcaa gtattgtgta cgaggcggcc gatgccatcc tgctcgagat gagcacgaat    660
cctaaacctc aaagaaaaac caaacgtaac accaaccgtc gcccacagga cgtcaagttc    720
ccgggtggcg gtcagatcgt tggtggagtt tacttgttgc cgcgcagggg ccctagattg    780
ggtgtgcgcg cgacgagggg atcccgggca caccatcacc atcaccatta agatccggtg    840
gatgaccttt tgaatgacct taatagatt atattactaa ttaattgggg accctagagg    900 tcccttttttt atttttaaaaa ttttttcaca aaacggttta caagcataaa gctctgcatt    960
aatgaatcgg ccaacgcgcg gggagaggcg gtttgcgtat tgggcgctct tccgcttcct   1020
cgctcactga ctcgctgcgc tcggtcgttc ggctgcggcg agcggtatca gctcactcaa   1080
aggcggtaat acggttatcc acagaatcag gggataacgc aggaaagaac atgtgagcaa   1140
aaggccagca aaaggccagg aaccgtaaaa aggccgcgtt gctggcgttt ttccataggc   1200 tccgccccc tgacgagcat cacaaaaatc gacgctcaag tcagaggtgg cgaaacccga   1260
caggactata aagataccag gcgtttcccc ctggaagctc cctcgtgcgc tctcctgttc   1320
cgaccctgcc gcttaccgga tacctgtccg cctttctccc ttcgggaagc gtggcgcttt   1380
ctcatagctc acgctgtagg tatctcagtt cggtgtaggt cgttcgctcc aagctgggct   1440
gtgtgcacga accccccgtt cagcccgacc gctgcgcctt atccggtaac tatcgtcttg   1500
agtccaaccc ggtaagacac gacttatcgc cactggcagc agccactggt aacaggatta   1560
gcagagcgag gtatgtaggc ggtgctacag agttcttgaa gtggtggcct aactacggct   1620
acactagaag gacagtattt ggtatctgcg ctctgctgaa gccagttacc ttcggaaaaa   1680
gagttggtag ctcttgatcc ggcaaacaaa ccaccgctgg tagcggtggt ttttttgttt   1740
gcaagcagca gattacgcgc agaaaaaaag gatctcaaga agatcctttg atcttttcta   1800
cggggtctga cgctcagtgg aacgaaaact cacgttaagg attttggtc atgagattat   1860 caaaaaggat cttcacctag atccttttaa attaaaaatg aagttttaaa tcaatctaaa   1920
gtatatatga gtaaacttgg tctgacagtt accaatgctt aatcagtgag gcacctatct   1980
cagcgatctg tctatttcgt tcatccatag ttgcctgact ccccgtcgtg tagataacta   2040
cgatacggga gggcttacca tctggcccca gtgctgcaat gataccgcga acccacgct   2100 caccggctcc agatttatca gcaataaacc agccagccgg aagggccgag cgcagaagtg   2160
gtcctgcaac tttatccgcc tccatccagt ctattaattg ttgccgggaa gctagagtaa   2220
gtagttcgcc agttaatagt ttgcgcaacg ttgttgccat tgctacaggc atcgtggtgt   2280
cacgctcgtc gtttggtatg gcttcattca gctccggttc ccaacgatca aggcgagtta   2340
catgatcccc catgttgtgc aaaaaagcgg ttagctcctt cggtcctccg atcgttgtca   2400
gaagtaagtt ggccgcagtg ttatcactca tggttatggc agcactgcat aattctctta   2460
ctgtcatgcc atccgtaaga tgcttttctg tgactggtga gtactcaacc aagtcattct   2520
gagaatagtg tatgcggcga ccgagttgct cttgcccggc gtcaatacgg gataataccg   2580
cgccacatag cagaacttta aaagtgctca tcattggaaa acgttcttcg ggcgaaaac   2640 tctcaaggat cttaccgctg ttgagatcca gttcgatgta acccactcgt gcacccaact   2700
```

```
gatcttcagc atctttact ttcaccagcg tttctgggtg agcaaaaaca ggaaggcaaa    2760
atgccgcaaa aagggaata agggcgacac ggaaatgttg aatactcata ctcttccttt    2820
ttcaatatta ttgaagcatt tatcagggtt attgtctcat gagcggatac atatttgaat    2880
gtatttagaa aaataaacaa ataggggttc cgcgcacatt tccccgaaaa gtgccacctg    2940
acgtctaaga aaccattatt atcatgacat taacctataa aaataggcgt atcacgaggc    3000
cctttcgtct tcaagaatta attcgggaat aagattcaac gccagtcccg aacgtgaaat    3060
ttcctctctt gctggcgcga ttgcagctgt ggtgtcatgg tcggtgatcg ccagggtgcc    3120
gacgcgcatc tcgactgcac ggtgcaccaa tgcttctggc gtcaggcagc catcggaagc    3180
tgtggtatgg ctgtgcaggt cgtaaatcac tgcataattc gtgtcgctca aggcgcactc    3240
ccgttctgga taatgttttt tgcgccgaca tcataacggt tctggcaaat attctgaaat    3300
gagctgttga caattaatca tcgaactagt taactagtac gcaagttcac gtaaaaaggg    3360
tatcgattcc                                                          3370
```

<210> SEQ ID NO 9
<211> LENGTH: 276
<212> TYPE: PRT
<213> ORGANISM: Artificial Sequence
<220> FEATURE:
<223> OTHER INFORMATION: Artificial Sequence Description: Sequence corresponding to Coq1 antigen

<400> SEQUENCE: 9

Met Val Asp Lys Arg Met Ala Leu Val Glu Leu Lys Val Pro Asp Ile
 1               5                   10                  15

Gly Gly His Glu Asn Val Asp Ile Ile Ala Val Glu Val Asn Val Gly
                20                  25                  30

Asp Thr Ile Ala Val Asp Asp Thr Leu Ile Thr Leu Asp Leu Asp Met
            35                  40                  45

Ser Thr Asn Pro Lys Pro Gln Arg Lys Thr Lys Arg Asn Thr Asn Arg
        50                  55                  60

Arg Pro Gln Asp Val Lys Phe Pro Gly Gly Gly Gln Ile Val Gly Gly
    65                  70                  75                  80

Val Tyr Leu Leu Pro Arg Arg Gly Pro Arg Leu Gly Val Arg Ala Thr
                85                  90                  95

Arg Lys Leu Ser Gln Lys Ile Gln Leu Val Asn Thr Asn Gly Ser Trp
            100                 105                 110

His Ile Asn Arg Thr Ala Leu Asn Cys Asn Asp Ser Leu Gln Thr Gly
        115                 120                 125

Phe Leu Ala Ala Leu Phe Tyr Val His Arg Phe Asn Ser Ser Gly Cys
    130                 135                 140

Ser Asp Arg Met Ala Ser Cys Arg Pro Ile Asp Thr Phe Asp Gln Gly
145                 150                 155                 160

Trp Gly Pro Ile Thr Tyr Ala Glu Pro Arg Ser Leu Asp Gln Arg Pro
                165                 170                 175

Tyr Cys Trp His Tyr Ala Pro Gln Pro Cys Gly Ile Val Pro Ala Ala
            180                 185                 190

Glu Val Cys Gly Pro Val Tyr Cys Phe Thr Pro Ser Pro Val Val Val
        195                 200                 205

Gly Thr Thr Asp Arg Ser Gly Val Pro Thr Tyr Asn Trp Gly Glu Asn
    210                 215                 220

Glu Thr Asp Val Leu Leu Leu Thr Arg Ala Ser Ala Tyr Glu Val Arg

```
                  225                 230                 235                 240
        Asn Ala Ser Gly Val Tyr His Val Thr Asn Asp Cys Ser Asn Ser Ser
                        245                 250                 255

Ile Val Tyr Glu Ala Asp Asp Met Ile Met Gly Ser Arg Ala His His
                        260                 265                 270

His His His His
                275

<210> SEQ ID NO 10
<211> LENGTH: 276
<212> TYPE: PRT
<213> ORGANISM: Artificial Sequence
<220> FEATURE:
<223> OTHER INFORMATION: Artificial Sequence Description: Sequence
      corresponding to Eq1 antigen

<400> SEQUENCE: 10

Met Val Asp Lys Arg Met Ala Leu Val Glu Leu Lys Val Pro Asp Ile
        1               5                   10                  15

Gly Gly His Glu Asn Val Asp Ile Ile Ala Val Glu Val Asn Val Gly
                        20                  25                  30

Asp Thr Ile Ala Val Asp Asp Thr Leu Ile Thr Leu Asp Leu Asp Ser
                        35                  40                  45

Gln Lys Ile Gln Leu Val Asn Thr Asn Gly Ser Trp His Ile Asn Arg
                50                  55                  60

Thr Ala Leu Asn Cys Asn Asp Ser Leu Gln Thr Gly Phe Leu Ala Ala
        65                  70                  75                  80

Leu Phe Tyr Val His Arg Phe Asn Ser Ser Gly Cys Ser Asp Arg Met
                        85                  90                  95

Ala Ser Cys Arg Pro Ile Asp Thr Phe Asp Gln Gly Trp Gly Pro Ile
                        100                 105                 110

Thr Tyr Ala Glu Pro Arg Ser Leu Asp Gln Arg Pro Tyr Cys Trp His
                        115                 120                 125

Tyr Ala Pro Gln Pro Cys Gly Ile Val Pro Ala Ala Glu Val Cys Gly
                130                 135                 140

Pro Val Tyr Cys Phe Thr Pro Ser Pro Val Val Val Gly Thr Thr Asp
        145                 150                 155                 160

Arg Ser Gly Val Pro Thr Tyr Asn Trp Gly Glu Asn Glu Thr Asp Val
                        165                 170                 175

Leu Leu Leu Lys Ala Ser Ser Ala Tyr Glu Val Arg Asn Ala Ser Gly
                        180                 185                 190

Val Tyr His Val Thr Asn Asp Cys Ser Asn Ser Ser Ile Val Tyr Glu
                        195                 200                 205

Ala Asp Asp Met Ile Met Leu Glu Met Ser Thr Asn Pro Lys Pro Gln
                210                 215                 220

Arg Lys Thr Lys Arg Asn Thr Asn Arg Arg Pro Gln Asp Val Lys Phe
        225                 230                 235                 240

Pro Gly Gly Gly Gln Ile Val Gly Gly Val Tyr Leu Leu Pro Arg Arg
                        245                 250                 255

Gly Pro Arg Leu Gly Val Arg Ala Thr Arg Gly Ser Arg Ala His His
                        260                 265                 270

His His His His
                275

<210> SEQ ID NO 11
<211> LENGTH: 276
```

```
<212> TYPE: PRT
<213> ORGANISM: Artificial Sequence
<220> FEATURE:
<223> OTHER INFORMATION: Artificial Sequence Description: Sequence
      corresponding to E1q1 antigen

<400> SEQUENCE: 11

Met Val Asp Lys Arg Met Ala Leu Val Glu Leu Lys Val Pro Asp Ile
 1               5                  10                  15

Gly Gly His Glu Asn Val Asp Ile Ile Ala Val Glu Val Asn Val Gly
             20                  25                  30

Asp Thr Ile Ala Val Asp Asp Thr Leu Ile Thr Leu Asp Leu Asp Ser
         35                  40                  45

Ala Tyr Glu Val Arg Asn Ala Ser Gly Val Tyr His Val Thr Asn Asp
     50                  55                  60

Cys Ser Asn Ser Ser Ile Val Tyr Glu Ala Asp Asp Met Ile Met Lys
 65                  70                  75                  80

Ala Ser Ser Gln Lys Ile Gln Leu Val Asn Thr Asn Gly Ser Trp His
                 85                  90                  95

Ile Asn Arg Thr Ala Leu Asn Cys Asn Asp Ser Leu Gln Thr Gly Phe
            100                 105                 110

Leu Ala Ala Leu Phe Tyr Val His Arg Phe Asn Ser Ser Gly Cys Ser
        115                 120                 125

Asp Arg Met Ala Ser Cys Arg Pro Ile Asp Thr Phe Asp Gln Gly Trp
    130                 135                 140

Gly Pro Ile Thr Tyr Ala Glu Pro Arg Ser Leu Asp Gln Arg Pro Tyr
145                 150                 155                 160

Cys Trp His Tyr Ala Pro Gln Pro Cys Gly Ile Val Pro Ala Ala Glu
                165                 170                 175

Val Cys Gly Pro Val Tyr Cys Phe Thr Pro Ser Pro Val Val Val Gly
            180                 185                 190

Thr Thr Asp Arg Ser Gly Val Pro Thr Tyr Asn Trp Gly Glu Asn Glu
        195                 200                 205

Thr Asp Val Leu Leu Leu Leu Glu Met Ser Gly Asn Pro Lys Pro Gln
    210                 215                 220

Arg Lys Thr Lys Arg Asn Thr Asn Arg Arg Pro Gln Asp Val Lys Phe
225                 230                 235                 240

Pro Gly Gly Gly Gln Ile Val Gly Gly Val Tyr Leu Leu Pro Arg Arg
                245                 250                 255

Gly Pro Arg Leu Gly Val Arg Ala Thr Arg Gly Ser Arg Ala His His
            260                 265                 270

His His His His
        275

<210> SEQ ID NO 12
<211> LENGTH: 333
<212> TYPE: PRT
<213> ORGANISM: Artificial Sequence
<220> FEATURE:
<223> OTHER INFORMATION: Artificial Sequence Description: Sequence
      corresponding to NSEq2 antigen

<400> SEQUENCE: 12

Met Val Asp Lys Arg Met Ala Leu Val Glu Leu Lys Val Pro Asp Ile
 1               5                  10                  15

Gly Gly His Glu Asn Val Asp Ile Ile Ala Val Glu Val Asn Val Gly
             20                  25                  30
```

Asp Thr Ile Ala Val Asp Asp Thr Leu Ile Thr Leu Asp Leu Asp Ser
            35                  40                  45

Gln Lys Ile Gln Leu Val Asn Thr Asn Gly Ser Trp His Ile Asn Arg
 50                  55                  60

Thr Ala Leu Asn Cys Asn Asp Ser Leu Gln Thr Gly Phe Leu Ala Ala
 65                  70                  75                  80

Leu Phe Tyr Val His Arg Phe Asn Ser Ser Gly Cys Ser Asp Arg Met
                85                  90                  95

Ala Ser Cys Arg Pro Ile Asp Thr Phe Asp Gln Gly Trp Gly Pro Ile
            100                 105                 110

Thr Tyr Ala Glu Pro Arg Ser Leu Asp Gln Arg Pro Tyr Cys Trp His
            115                 120                 125

Tyr Ala Pro Gln Pro Cys Gly Ile Val Pro Ala Ala Glu Val Cys Gly
130                 135                 140

Pro Val Tyr Cys Phe Thr Pro Ser Pro Val Val Val Gly Thr Thr Asp
145                 150                 155                 160

Arg Ser Gly Val Pro Thr Tyr Asn Trp Gly Glu Asn Glu Thr Asp Val
                165                 170                 175

Leu Leu Leu Lys Ala Ser Ser Ala Tyr Glu Val Arg Asn Ala Ser Gly
            180                 185                 190

Val Tyr His Val Thr Asn Asp Cys Ser Asn Ser Ser Ile Val Tyr Glu
            195                 200                 205

Ala Asp Asp Met Ile Met Leu Glu Tyr Leu Val Ala Tyr Gln Ala Thr
            210                 215                 220

Val Cys Ala Arg Ala Gln Ala Pro Pro Ser Trp Ala Ala Tyr Gly
225                 230                 235                 240

Tyr Lys Val Ile Val Leu Asn Pro Arg Val Ala Ser Thr Leu Ala Ala
                245                 250                 255

Tyr Leu Pro Glu Tyr Val Ile Met Val Lys Leu Pro Ser Arg Ala Leu
            260                 265                 270

Glu Met Ser Thr Asn Pro Lys Pro Gln Arg Lys Thr Lys Arg Asn Thr
            275                 280                 285

Asn Arg Arg Pro Gln Asp Val Lys Phe Pro Gly Gly Gly Gln Ile Val
290                 295                 300

Gly Gly Val Tyr Leu Leu Pro Arg Arg Gly Pro Arg Leu Gly Val Arg
305                 310                 315                 320

Ala Thr Arg Gly Ser Arg Ala His His His His His His
                325                 330

<210> SEQ ID NO 13
<211> LENGTH: 341
<212> TYPE: PRT
<213> ORGANISM: Artificial Sequence
<220> FEATURE:
<223> OTHER INFORMATION: Artificial Sequence Description: Sequence
      corresponding to EqNSb antigen

<400> SEQUENCE: 13

Met Val Asp Lys Arg Met Ala Leu Val Glu Leu Lys Val Pro Asp Ile
 1               5                  10                  15

Gly Gly His Glu Asn Val Asp Ile Ile Ala Val Glu Val Asn Val Gly
                20                  25                  30

Asp Thr Ile Ala Val Asp Asp Thr Leu Ile Thr Leu Asp Leu Asp Ser
            35                  40                  45

Gln Lys Ile Gln Leu Val Asn Thr Asn Gly Ser Trp His Ile Asn Arg
 50                  55                  60

Thr Ala Leu Asn Cys Asn Asp Ser Leu Gln Thr Gly Phe Leu Ala Ala
65                  70                  75                  80

Leu Phe Tyr Val His Arg Phe Asn Ser Ser Gly Cys Ser Asp Arg Met
                85                  90                  95

Ala Ser Cys Arg Pro Ile Asp Thr Phe Asp Gln Gly Trp Gly Pro Ile
            100                 105                 110

Thr Tyr Ala Glu Pro Arg Ser Leu Asp Gln Arg Pro Tyr Cys Trp His
        115                 120                 125

Tyr Ala Pro Gln Pro Cys Gly Ile Val Pro Ala Ala Glu Val Cys Gly
130                 135                 140

Pro Val Tyr Cys Phe Thr Pro Ser Pro Val Val Gly Thr Thr Asp
145                 150                 155                 160

Arg Ser Gly Val Pro Thr Tyr Asn Trp Gly Glu Asn Glu Thr Asp Val
                165                 170                 175

Leu Leu Leu Lys Ala Ser Ser Ala Tyr Glu Val Arg Asn Ala Ser Gly
            180                 185                 190

Val Tyr His Val Thr Asn Asp Cys Ser Asn Ser Ser Ile Val Tyr Glu
        195                 200                 205

Ala Asp Asp Met Ile Met Leu Glu Arg Ser Gly Arg His Leu Ile Phe
210                 215                 220

Cys His Ser Lys Lys Lys Cys Asp Glu Leu Ala Thr Lys Leu Ala Ala
225                 230                 235                 240

Tyr Tyr Leu Val Ala Tyr Gln Ala Thr Val Cys Ala Arg Ala Gln Ala
                245                 250                 255

Pro Pro Pro Ser Trp Ala Ala Tyr Gly Tyr Lys Val Ile Val Leu Asn
            260                 265                 270

Pro Arg Val Ala Ser Thr Leu Leu Glu Met Ser Thr Asn Pro Lys Pro
        275                 280                 285

Gln Arg Lys Thr Lys Arg Asn Thr Asn Arg Arg Pro Gln Asp Val Lys
290                 295                 300

Phe Pro Gly Gly Gly Gln Ile Val Gly Gly Val Tyr Leu Leu Pro Arg
305                 310                 315                 320

Arg Gly Pro Arg Leu Gly Val Arg Ala Thr Arg Gly Ser Arg Ala His
                325                 330                 335

His His His His
        340

<210> SEQ ID NO 14
<211> LENGTH: 454
<212> TYPE: PRT
<213> ORGANISM: Artificial Sequence
<220> FEATURE:
<223> OTHER INFORMATION: Artificial Sequence Description: Sequence
      corresponding to EqNS3 antigen

<400> SEQUENCE: 14

Met Val Asp Lys Arg Met Ala Leu Val Glu Leu Lys Val Pro Asp Ile
1               5                   10                  15

Gly Gly His Glu Asn Val Asp Ile Ile Ala Val Glu Val Asn Val Gly
            20                  25                  30

Asp Thr Ile Ala Val Asp Asp Thr Leu Ile Thr Leu Asp Ser
        35                  40                  45

Gln Lys Ile Gln Leu Val Asn Thr Asn Gly Ser Trp His Ile Asn Arg
50                  55                  60

Thr Ala Leu Asn Cys Asn Asp Ser Leu Gln Thr Gly Phe Leu Ala Ala

```
              65                  70                  75                  80
        Leu Phe Tyr Val His Arg Phe Asn Ser Ser Gly Cys Ser Asp Arg Met
                            85                  90                  95
        Ala Ser Cys Arg Pro Ile Asp Thr Phe Asp Gln Gly Trp Gly Pro Ile
                        100                 105                 110
        Thr Tyr Ala Glu Pro Arg Ser Leu Asp Gln Arg Pro Tyr Cys Trp His
                    115                 120                 125
        Tyr Ala Pro Gln Pro Cys Gly Ile Val Pro Ala Glu Val Cys Gly
        130                 135                 140
        Pro Val Tyr Cys Phe Thr Pro Ser Pro Val Val Gly Thr Thr Asp
        145                 150                 155                 160
        Arg Ser Gly Val Pro Thr Tyr Asn Trp Gly Glu Asn Glu Thr Asp Val
                        165                 170                 175
        Leu Leu Leu Lys Ala Ser Ser Ala Tyr Glu Val Arg Asn Ala Ser Gly
                    180                 185                 190
        Val Tyr His Val Thr Asn Asp Cys Ser Asn Ser Ser Ile Val Tyr Glu
                195                 200                 205
        Ala Asp Asp Met Ile Met Leu Glu Arg Ser Ala Ala Tyr Ala Ala Gln
        210                 215                 220
        Gly Tyr Lys Val Leu Val Leu Asn Pro Ser Val Ala Ala Thr Leu Gly
        225                 230                 235                 240
        Phe Gly Ala Tyr Met Ser Lys Ala His Gly Ile Asp Pro Asn Ile Arg
                        245                 250                 255
        Thr Gly Val Arg Thr Ile Thr Thr Gly Ser Pro Ile Thr Tyr Ser Thr
                    260                 265                 270
        Tyr Gly Lys Phe Leu Ala Asp Gly Gly Cys Ser Gly Gly Ala Tyr Asp
                275                 280                 285
        Ile Ile Ile Cys Asp Glu Cys His Ser Thr Asp Ala Thr Ser Ile Leu
                290                 295                 300
        Gly Ile Gly Thr Val Leu Asp Gln Ala Glu Thr Ala Gly Ala Arg Leu
        305                 310                 315                 320
        Val Val Leu Ala Thr Ala Thr Pro Pro Gly Ser Val Thr Val Pro His
                        325                 330                 335
        Pro Asn Ile Glu Glu Val Ala Leu Ser Thr Thr Gly Glu Ile Pro Phe
                    340                 345                 350
        Tyr Gly Lys Ala Ile Pro Leu Glu Val Ile Lys Gly Gly Arg His Leu
                355                 360                 365
        Ile Phe Cys His Ser Lys Lys Lys Cys Asp Glu Leu Ala Ala Lys Leu
            370                 375                 380
        Val Ala Leu Gly Ile Asn Ala Val Leu Glu Met Ser Thr Asn Pro Lys
        385                 390                 395                 400
        Pro Gln Arg Lys Thr Lys Arg Asn Thr Asn Arg Arg Pro Gln Asp Val
                        405                 410                 415
        Lys Phe Pro Gly Gly Gly Gln Ile Val Gly Gly Val Tyr Leu Leu Pro
                    420                 425                 430
        Arg Arg Gly Pro Arg Leu Gly Val Arg Ala Thr Arg Gly Ser Arg Ala
                435                 440                 445
        His His His His His His
            450

<210> SEQ ID NO 15
<211> LENGTH: 292
<212> TYPE: PRT
<213> ORGANISM: Artificial Sequence
```

```
<220> FEATURE:
<223> OTHER INFORMATION: Artificial Sequence Description: Sequence
      corresponding to EqP1 antigen

<400> SEQUENCE: 15

Met Val Asp Lys Arg Met Ala Leu Val Glu Leu Lys Val Pro Asp Ile
1               5                   10                  15

Gly Gly His Glu Asn Val Asp Ile Ile Ala Val Glu Val Asn Val Gly
                20                  25                  30

Asp Thr Ile Ala Val Asp Thr Leu Ile Thr Leu Asp Leu Asp Ser
            35                  40                  45

Gln Lys Ile Gln Leu Val Asn Thr Asn Gly Ser Trp His Ile Asn Arg
 50                  55                  60

Thr Ala Leu Asn Cys Asn Asp Ser Leu Gln Thr Gly Phe Leu Ala Ala
65                  70                  75                  80

Leu Phe Tyr Val His Arg Phe Asn Ser Ser Gly Cys Ser Asp Arg Met
                85                  90                  95

Ala Ser Cys Arg Pro Ile Asp Thr Phe Asp Gln Gly Trp Gly Pro Ile
            100                 105                 110

Thr Tyr Ala Glu Pro Arg Ser Leu Asp Gln Arg Pro Tyr Cys Trp His
        115                 120                 125

Tyr Ala Pro Gln Pro Cys Gly Ile Val Pro Ala Ala Glu Val Cys Gly
    130                 135                 140

Pro Val Tyr Cys Phe Thr Pro Ser Pro Val Val Val Gly Thr Thr Asp
145                 150                 155                 160

Arg Ser Gly Val Pro Thr Tyr Asn Trp Gly Glu Asn Glu Thr Asp Val
                165                 170                 175

Leu Leu Leu Lys Ala Ser Ser Ala Tyr Glu Val Arg Asn Ala Ser Gly
            180                 185                 190

Val Tyr His Val Thr Asn Asp Cys Ser Asn Ser Ser Ile Val Tyr Glu
        195                 200                 205

Ala Asp Asp Met Ile Met Leu Glu Leu Pro Glu Tyr Val Ile Met Val
    210                 215                 220

Lys Leu Pro Ser Arg Ala Leu Glu Met Ser Thr Asn Pro Lys Pro Gln
225                 230                 235                 240

Arg Lys Thr Lys Arg Asn Thr Asn Arg Arg Pro Gln Asp Val Lys Phe
                245                 250                 255

Pro Gly Gly Gly Gln Ile Val Gly Gly Val Tyr Leu Leu Pro Arg Arg
            260                 265                 270

Gly Pro Arg Leu Gly Val Arg Ala Thr Arg Gly Ser Arg Ala His His
        275                 280                 285

His His His His
    290

<210> SEQ ID NO 16
<211> LENGTH: 276
<212> TYPE: PRT
<213> ORGANISM: Artificial Sequence
<220> FEATURE:
<223> OTHER INFORMATION: Artificial Sequence Description: Sequence
      corresponding to Eq1b antigen

<400> SEQUENCE: 16

Met Val Asp Lys Arg Met Ala Leu Val Glu Leu Lys Val Pro Asp Ile
1               5                   10                  15

Gly Gly His Glu Asn Val Asp Ile Ile Ala Val Glu Val Asn Val Gly
                20                  25                  30
```

```
Asp Thr Ile Ala Val Asp Asp Thr Leu Ile Thr Leu Asp Leu Asp Lys
        35                  40                  45

Gln Asn Ile Gln Leu Ile Asn Thr Asn Gly Ser Trp His Ile Asn Ser
        50                  55                  60

Thr Ala Leu Asn Cys Asn Glu Ser Leu Asn Thr Gly Trp Leu Ala Gly
 65                  70                  75                  80

Leu Phe Tyr Gln His Lys Phe Asn Ser Ser Gly Cys Pro Glu Arg Leu
                    85                  90                  95

Ala Ser Cys Arg Arg Leu Thr Asp Phe Ala Gln Gly Trp Gly Pro Ile
                100                 105                 110

Ser Tyr Ala Asn Gly Ser Gly Leu Asp Glu Arg Pro Tyr Cys Trp His
                115                 120                 125

Tyr Pro Pro Arg Pro Cys Gly Ile Val Pro Ala Lys Ser Val Cys Gly
            130                 135                 140

Pro Val Tyr Cys Phe Thr Pro Ser Pro Val Val Val Gly Thr Thr Asp
145                 150                 155                 160

Arg Ser Gly Ala Pro Thr Tyr Ser Trp Gly Ala Asn Asp Thr Asp Val
                    165                 170                 175

Phe Val Leu Lys Ala Ser Ser Ala Tyr Gln Val Arg Asn Ser Ser Gly
                180                 185                 190

Leu Tyr His Val Thr Asn Asp Cys Pro Asn Ser Ser Ile Val Tyr Glu
                195                 200                 205

Ala Ala Asp Ala Ile Leu Leu Glu Met Ser Thr Asn Pro Lys Pro Gln
            210                 215                 220

Arg Lys Thr Lys Arg Asn Thr Asn Arg Arg Pro Gln Asp Val Lys Phe
225                 230                 235                 240

Pro Gly Gly Gly Gln Ile Val Gly Gly Val Tyr Leu Leu Pro Arg Arg
                    245                 250                 255

Gly Pro Arg Leu Gly Val Arg Ala Thr Arg Gly Ser Arg Ala His His
                260                 265                 270

His His His His
        275

<210> SEQ ID NO 17
<211> LENGTH: 14
<212> TYPE: PRT
<213> ORGANISM: Artificial Sequence
<220> FEATURE:
<223> OTHER INFORMATION: Artificial Sequence Description: Sequence
      corresponding to P1M artificial epitope

<400> SEQUENCE: 17

Leu Pro Glu Tyr Val Ile Met Val Lys Leu Pro Ser Arg Ala
 1               5                  10

<210> SEQ ID NO 18
<211> LENGTH: 15
<212> TYPE: PRT
<213> ORGANISM: Artificial Sequence
<220> FEATURE:
<223> OTHER INFORMATION: Artificial Sequence Description: Sequence
      corresponding to P2B artificial epitope

<400> SEQUENCE: 18

Gly Tyr Lys Val Ile Val Leu Asn Pro Arg Val Ala Ser Thr Leu
 1               5                  10                  15
```